United States Patent
Wu et al.

(10) Patent No.: US 10,738,275 B2
(45) Date of Patent: Aug. 11, 2020

(54) *PAENIBACILLUS* SP. STRAIN, CULTIVATION METHOD AND USE OF THE SAME

(71) Applicant: BRIGHT DAIRY & FOOD CO., LTD, Shanghai (CN)

(72) Inventors: Zhengjun Wu, Shanghai (CN); Benheng Guo, Shanghai (CN); Caixia Gao, Shanghai (CN); Zhenmin Liu, Shanghai (CN); Feng Hang, Shanghai (CN); Jin Han, Shanghai (CN)

(73) Assignee: BRIGHT DAIRY & FOOD CO., LTD., Shanghai (CN)

( * ) Notice: Subject to any disclaimer, the term of this patent is extended or adjusted under 35 U.S.C. 154(b) by 0 days.

(21) Appl. No.: 16/137,991

(22) Filed: Sep. 21, 2018

(65) Prior Publication Data

US 2019/0093067 A1    Mar. 28, 2019

Related U.S. Application Data

(62) Division of application No. 15/109,133, filed on Jun. 30, 2016, now Pat. No. 10,113,145.

(51) Int. Cl.
| | | |
|---|---|---|
| *C12N 1/20* | (2006.01) | |
| *A61K 31/715* | (2006.01) | |
| *C12P 19/04* | (2006.01) | |
| *C12R 1/01* | (2006.01) | |
| *C08B 37/00* | (2006.01) | |

(52) U.S. Cl.
CPC ............ *C12N 1/20* (2013.01); *A61K 31/715* (2013.01); *C08B 37/006* (2013.01); *C12P 19/04* (2013.01); *C12R 1/01* (2013.01)

(58) Field of Classification Search
None
See application file for complete search history.

(56) References Cited

U.S. PATENT DOCUMENTS

| | | | | |
|---|---|---|---|---|
| 9,574,214 B2* | 2/2017 | Um | ............... | C12P 19/02 |
| 10,113,145 B2* | 10/2018 | Wu | ............... | C12P 19/04 |
| 2012/0141423 A1* | 6/2012 | Yousef | ............... | A61K 35/74 |
| | | | | 424/93.4 |
| 2014/0322273 A1* | 10/2014 | Ai | ............... | C12R 1/25 |
| | | | | 424/234.1 |
| 2014/0348878 A1* | 11/2014 | Ai | ............... | C12R 1/24 |
| | | | | 424/282.1 |
| 2017/0233694 A1* | 8/2017 | Wu | ............... | C12P 19/04 |
| | | | | 514/54 |
| 2019/0093067 A1* | 3/2019 | Wu | ............... | C12N 1/20 |
| 2019/0290675 A1* | 9/2019 | Gibson | ............... | A61K 9/0029 |

FOREIGN PATENT DOCUMENTS

| | | | |
|---|---|---|---|
| CN | 104231106 A | * | 12/2014 |
| CN | 104911167 A | * | 9/2015 |
| CN | 105274079 A | * | 1/2016 |
| CN | 105349513 A | * | 2/2016 |
| CN | 108641987 A | * | 10/2018 |
| WO | WO-2015101116 A1 | * | 7/2015 |

OTHER PUBLICATIONS

Hang et al, International J. Biological Macromolecules, 2017, 95:1082-1090. available online: Nov. 2, 2016 (Year: 2017).*
Xu et al, Carbohydrate Polymers, 2016, 144:178-186. Available online: Feb. 18, 2016 (Year: 2016).*
Raza et al, Bioresource Technology, 2011, 102/10:6095-6103 Abstract Only (Year: 2011).*
Gong et al, Journal of Environmental Science and Health, Part A: Toxic/Hazardous Substances & Environmental Engineering (2003), A38(4):657-669. abstract only (Year: 2003).*
Zeilger et al, The Family Paenibacillaceae, Bacillus, Genetic Stock Center Catalog of Strains, Part 5, 2013, www.bgsc.org (Year: 2013).*
Liu et al, Carbohydrate Polymers, 2009, 78:275-281 (Year: 2009).*
Liu et al, Carbohydrate Polymers, 2010, 79:206-213 (Year: 2010).*
Rutering et al, Carbohydrate Polymers, 2016, 148:326-334 (Year: 2016).*
Seo et al, Journal of Microbiology and Biotechnology, Dec. 1999, 9/6:820-825. abstract only (Year: 1999).*
Yegorenkova et al, Microbiology, 2008, 77/5:553-558 (Year: 2008).*
Li et al, Bioresource Technology, 2013, 134:87-93. (Year: 2013).*
Liu et al, Nongyaoxue Xuebao, Dec. 2011, 13/6:603-607. abstract only (Year: 2011).*

* cited by examiner

*Primary Examiner* — Nita M. Minnifield
(74) *Attorney, Agent, or Firm* — Bayramoglu Law Offices LLC

(57) ABSTRACT

Provided are a new *Paenibacillus* sp. strain, the deposit number of which is CGMCC No. 8333, and a method for culturing the exopolysaccharide; and an exopolysaccharide having a structural formula as shown in formula (I) being produced by the strain, as well as a production method thereof and its use in promoting the propagation of *bifidobacterium*. The exopolysaccharide shown by formula (I) has a moderate degree of polymerization (DP=15-30) and has the functions of promoting the propagation of *bifidobacterium*, as well as adjusting human intestinal microflora.

16 Claims, 7 Drawing Sheets

Specification includes a Sequence Listing.

(a) fructose (b) Hydrolysate of purified BD3526 EPS

BD3526EPS FOS blank control group

SEQUENCE LISTING

```
<160> NUMBER OF SEQ ID NOS: 6

<210> SEQ ID NO 1
<211> LENGTH: 1430
<212> TYPE: DNA
<213> ORGANISM: Paenibacillus sp.

<400> SEQUENCE: 1
tgcagtcgag cggagttgat agagtgcttg cactcttgag acttagcggc ggacgggtga      60
gtaacacgta ggcaacctgc ccctcagact gggataacta ccggaaacgg tagctaatac     120
cggataatcg ttttcttctc ctgaagagac cgggaaagac ggagcaatct gtcactgagg     180
gatgggcctg cggcgcatta gctagttggt ggggtaacgg ctcaccaagg cgacgatgcg     240
tagccgacct gagagggtga tcggccacac tgggactgag acacggccca gactcctacg     300
ggaggcagca gtagggaatc ttccgcaatg gacgaaagtc tgacggagca acgccgcgtg     360
```

```
agtgatgaag gttttcggat cgtaaagctc tgttgccagg gaagaacgtc ttctagagta      420
actgctagaa gagtgacggt acctgagaag aaagccccgg ctaactacgt gccagcagcc      480
gcggtaatac gtaggggggca agcgttgtcc ggaattattg ggcgtaaagc gcgcgcaggc     540
ggtcatttaa gtctggtgtt taatcccgaa gctcaacttc gggtcgcatc ggaaactgga      600
tgacttgagt gcagaagagg agagtggaat tccacgtgta gcggtgaaat gcgtagagat      660
gtggaggaac accagtggcg aaggcgactc tctgggctgt aactgacgct gaggcgcgaa      720
agcgtgggga gcaaacagga ttagatacc tggtagtcca cgccgtaaac gatgaatgct       780
aggtgttagg ggtttcgata cccttggtgc cgaagttaac acattaagca ttccgcctgg      840
ggagtacggt cgcaagactg aaactcaaag gaattgacgg ggacccgcac aagcagtgga      900
gtatgtggtt taattcgaag caacgcgaag aaccttacca ggtcttgaca tctgaatgac      960
cggtgcagag atgtaccttt tcttcggaac attcaagaca ggtggtgcat ggttgtcgtc     1020
agctcgtgtc gtgagatgtt gggttaagtc ccgcaacgag cgcaacccctt atgcttagtt    1080 gccagcacat catggtgggc actctaagca gactgccggt gacaaaccgg aggaaggtgg     1140
ggatgacgtc aaatcatcat gccccttatg acctgggcta cacacgtact acaatggtcg     1200
gtacaacggg aagcgaagcc gcgaggtgga gcgaatccta aaaagccgat ctcagttcgg     1260
attgcaggct gcaactcgcc tgcatgaagt cggaattgct agtaatcgcg gatcagcatg     1320
ccgcggtgaa tacgttcccg ggtcttgtac acaccgcccg tcacaccacg agagtttgca     1380
acacccgaag tcggtggggt aacccgcaag gagccagccg ccgaaggtgg                1430

<210> SEQ ID NO 2
<211> LENGTH: 16
<212> TYPE: DNA
<213> ORGANISM: Artificial Sequence
<220> FEATURE:
<223> OTHER INFORMATION: Primer

<400> SEQUENCE: 2
taccttgtta cgactt                                                       16

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
agagtttgat cctggctcag                                                   20

<210> SEQ ID NO 4
<211> LENGTH: 15
<212> TYPE: DNA
<213> ORGANISM: Artificial Sequence
<220> FEATURE:
<223> OTHER INFORMATION: Primer 357F

<400> SEQUENCE: 4
tacgggaggc agcag                                                        15

<210> SEQ ID NO 5
<211> LENGTH: 17
<212> TYPE: DNA
<213> ORGANISM: Artificial Sequence
<220> FEATURE:
```

-continued

```
<223> OTHER INFORMATION: Primer 518R

<400> SEQUENCE: 5
attaccgcgg ctgctgg                                                    17

<210> SEQ ID NO 6
<211> LENGTH: 42
<212> TYPE: DNA
<213> ORGANISM: Artificial Sequence
<220> FEATURE:
<223> OTHER INFORMATION: GC-clamp

<400> SEQUENCE: 6
cgcccgccgc gcgcggcggg cggggcgggg gcacgggggg cc                        42
```

PAENIBACILLUS SP. STRAIN, CULTIVATION METHOD AND USE OF THE SAME

CROSS REFERENCE TO RELATED APPLICATIONS

This application is a divisional application of Applicant Ser. No. 15/109,133 filed on Jun. 30, 2016, which is the national phase entry of International Application No. PCT/CN2014/091544, filed on Nov. 19, 2014, which is based upon and claims priority to Chinese patent application No. CN201310752153.7 with the filing date of Dec. 31, 2013. The contents of these related applications are incorporated herein by reference.

TECHNICAL FIELD

The present invention belongs to the field of microorganism, more specifically, relates to a new *Paenibacillus* sp. strain, the cultivation method and the use of the same.

BACKGROUND

In early research, *Paenibacillus* was classified into *Bacillus* based on the morphology. In 1994, by using PCR probe testing, Ash et al. analyzed the 16S rRNA sequences for different strains of *Bacillus*, and found that some of the *Bacillus* were significantly different from other *Bacillus* in terms of genotypic characteristics, and their 16S rRNA sequences were highly specific. Therefore, Ash separated 11 strains such as *Bacillus* polymyxin from *Bacillus* to form an independent genus, namely *Paenibacillus*.

The type strain of *Paenibacillus* is *Paenibacillus polmyxin* ATCC $842^T$, wherein the cells are in the shape of rods, the optimal growth temperature range is 28-30° C. and the main fatty acid is anteiso saturated fatty acid C15:0. The G+C content of *Paenibacillus* range is 45-54 mol %.

Generally, if the difference of G+C mol % between two strains is more than 5%, the two strains could be determined as different species (such determination can be made even if other characteristics are similar). The DNA homology analysis may finally determine the classification of the strains. It is also a way for determining new species. In optimum conditions, if the DNA homology is higher than 70%, the strains belong to the same species. If the DNA homology is higher than 20%, the strains belong to the same genus. Nowadays, it is believed that the effects of the combination of phenotype and DNA homology to classify species and genus are accurate and desirable.

Many microorganisms of *Paenibacillus* genus have the effects of disease-preventing and growth-promoting on plants. Therefore, they have a good usage potential in agricultural industry. The *Paenibacillus* may produce many kinds of bioactive substances such as enzymes, antibiotic substances, phytohormones, flocculants, and etc. Most of these active substances are proteins, polypeptides and polysaccharides, and etc.

Microbial extracellular polysaccharides (EPS for short), in some extent, have been demonstrated with the functions of anti-hyperlipidemia, immunoregulatory and anti-tumor and etc. Therefore, it may serve as the food additive. As the consumers are more and more concerned about the food safety issues, how to obtain new food additives (for example, thickener, emulsifier, stabilizer, etc) with a clear source, stable yield, and diverse functions attracted more and more attentions from researchers.

Levan is a type of fructans constituted of fructose units linked with β (2→6) fructoside bonds in main chain and with or without a few the branchs lingked by β (2→1) fructoside bonds. The levan with a low polymerization (DP for short) (DP=2-9) is usually called fructooligosaccharide. The levan with a DP range of 10-30 is usually called polyfructose. The levan with a DP higher than 40 is usually called high-polyfructose. Some levans that originates from microorganism have important biological activities such as anti-tumor, anti-virus, anti-hyperglycaemia, anti-hyperlipidemia and immunopotentiation, and thus they have a large usage potential in terms of medicines and functional foods.

There are three methods for producing levans in large quantities nowadays: the chemical synthesis method, the microbiological fermentation and enzymatic synthesis method. However, currently, the chemical synthesis method merely produces the trisaccharides formed by β-glycosidic bonds. Although both plants and microorganisms may produce levans, currently the levans produced by microorganism fermentation are all of high molecular weights with high polymerization degrees, usually $2 \times 10^6$-$100 \times 10^6$ Da and the DP is far more than 40. However, nowadays the yield and conversion rate of saccharose to manufacture levans from microbiological fermentation are usually low. Also, other products such as high polymers, glucoses, fructose, and fructooligosaccharides coexist in the fermentation broth. Thus, it is disadvantageous for large-scale purification of levans. On the other hand, the enzymatic synthesis method for producing levans requires certain conditions such as the particular pH, the temperature, and ect. to facilitate the reaction, which is complex and hard to control. Therefore, the strain with high productivity of levans and high saccharose conversion rate is the key for large-scale preparation of levans, especially for the levans with moderate and low polymerization.

SUMMARY

The purpose of the present invention is to disclose a new *Paenibacillus* sp. strain, the culture method for preparing levan, and the use of the same. The purpose of the present invention is realized by the following technical solutions.

The first technical solution of the present invention is a *Paenibacillus* sp. strain whose deposit number is CGMCC No. 8333.

The second technical solution of the present invention is the method for culturing *Paenibacillus* CGMCC No. 8333, which includes the following steps. The *Paenibacillus* CGMCC No. 8333 is inoculated onto the culture medium for culturing under 15-40° C. with a pH value of 5.5-8.5.

The temperature for culturing according to the present invention is 15-40° C., and preferably is 30° C.

The pH value for culturing according to the present invention is 5.5-8.5, and preferably is 6.0.

The cultivation according to the present invention may be various methods for culturing microorganisms, such as liquid culturing, solid culturing and semi-solid culturing. It may be shaking culturing. It also can be submerged fermentation in the fermentation tank. The shaking culturing is preferable.

The inoculation ratio of the culturing according to the present invention is conventional, preferably, 2%. The percentage is the volume percentage.

The culture medium according to the present invention is the conventional culture medium for *Paenibacillus*, preferably, TYC culture medium.

The culturing according to the present invention is the conventional culturing for *Paenibacillus*, and is preferably conducted under aerobic conditions.

The third technical solution of the present invention is the use of *Paenibacillus* CGMCC No. 8333 in preparing extracellular polysaccharide.

The fourth technical solution of the present invention is the extracellular polysaccharide of *Paenibacillus*. The structural formula of the extracellular polysaccharide is shown as Formula (1):

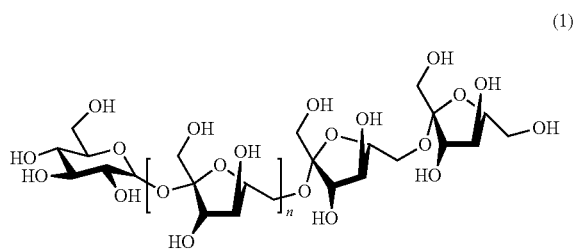

wherein, n=15-30.

Preferably, the extracellular polysaccharide has an average molecular weight distribution of 2500-5000 Da; and/or has the appearance of pure white filament or powder.

The extracellular polysaccharide is produced by conventional extracellular-polysaccharide-producing *Paenibacillus* strains in the literatures. Preferably, the extracellular polysaccharide is produced by *Paenibacillus bovis* sp. nov. BD3526 whose deposit number is CGMCC No. 8333, and produced by mutant strains or derivatives obtained from the original strain of *Paenibacillus* spp. BD3526.

The *Paenibacillus* spp. BD3526 with the deposit number of CGMCC No. 8333 has been deposited in China General Microbiological Culture Collection Center (CGMCC), and has been disclosed in Chinese patent application CN103740618A.

The fifth technical solution of the present invention is a method for preparing the extracellular polysaccharide of the *Paenibacillus*, including the following steps:

(1) The *Paenibacillus* CGMCC No. 8333 is cultivated to obtain a fermentation broth;

(2) The fermentation broth obtained in step (1) is heated for 10-30 minutes under 95-100° C. Once cooled down to 15-25° C., the pH value is adjusted to 4.4-4.8. It stands for 3-5 hours. It is centrifuged to obtain the supernatant. 80-100% ethanol solution is added at a volume 2-4 times as much as that of the supernatant. It stands overnight. It is centrifuged to collect the precipitates. Percentages refer to the mass percentages of the ethanol solution;

(3) The precipitate obtained in step (2) is dissolved in distilled water with the temperature of 50-80° C. to obtain the solution of precipitates with the concentration of 0.5-1.0%. Percentages refer to the mass-volume percentages of the solution of precipitates. Once the solution is cooled down to 20-25° C., trichloroacetic acid is added into the solution at a final percentage of 4%-10%. Percentages refer to the mass-volume percentages of the solution. The mixture is stored at 4-10° C. overnights centrifuged to obtain the supernatant. The supernatant is dialyzed with a membrane with a molecular weight cut-off of 1000 Da to obtain the retentate which contains extracellular polysaccharides.

(4) The retentate obtained in step (3) is dried to obtain the crude extracellular polysaccharides.

The step (1) is conducted by the *Paenibacillus* CGMCC No. 8333 to obtain the fermentation broth. Wherein, the fermentation of step (1) is the conventional fermentation in the art. Preferably, the fermentation is undertaken for 72 hours under 30° C. Preferably, the fermentation is conducted in the liquid polysaccharide-producing culture medium. The liquid polysaccharide-producing culture medium is composed of 10% saccharose, 1% casein tryptone, 0.5% yeast extract, 0.5% $K_2HPO_4$, 0.034% $CaCl_2$, and distilled water. Percentages refer to mass percentages of the liquid polysaccharide-producing culture medium. The inoculation ratio of the fermentation is the conventional inoculation ratio in the art, preferably, 1%. The percentage is the mass percentage of the liquid polysaccharide-producing culture medium.

The step (2) is heating the fermentation broth obtained in step (1) for 10-30 minutes under 95-100° C. Once cooled down to 15-25° C., the pH value is adjusted into 4.4-4.8. It stands for 3-5 hours. It is centrifuged to obtain supernatant. 80-100% ethanol solution is added with a volume 2-4 times as much as that of the supernatant. It stands overnight. It is centrifuged to collect the precipitates. Percentages refer to the mass percentages of the ethanol solution. Wherein, the centrifugal conditions in step (2) are conventional in the art, preferably, the centrifugation is conducted for 10 min at 14000 g. Preferably, the adjustment of pH value is adjusting the pH value to 4.6. Preferably, the ethanol solution in step (2) refers to a 95%-ethanol solution, wherein the percentage refers to the mass percentage of the ethanol solution. Preferably, the added volume of ethanol solution is 3 times as much as that of the supernatant.

The step (3) is dissolving the precipitates obtained in step (2) in distilled water with the temperature of 50-80° C. to obtain the solution of precipitates with the concentration of 0.5-1.0%. Percentages refer to the mass-volume percentages of the solution of precipitates. Once the solution is cooled down to 20-25° C., trichloroacetic acid is added into the solution to a final percentage of 4%-10%. Percentages refer to the mass-volume percentages of the solution. The mixture is stored at 4-10° C. overnights and centrifuged to obtain the supernatant. The supernatant is dialyzed with a membrane with a molecular weight cut-off of 1000 Da to obtain the retentate which contains extracellular polysaccharides. Wherein, the dissolution in step (3) preferably is dissolving the precipitates obtained in step (2) with distilled water with the temperature of 60° C. to obtain the solution of precipitates whose concentration is 0.8%. The percentage refers to the mass-volume percentage of the solution of precipitates. Once the solution is cooled down to 25° C., trichloroacetic acid is added into the solution to reach a final percentage of 4% of trichloroacetic acid. The percentage refers to the mass-volume percentage of the solution.

The step (4) is drying the retentate which contains extracellular polysaccharides obtained in step (3) to obtain the crude product of extracellular polysaccharides. Wherein, the drying in step (4) is the conventional drying in the art. Preferably, the drying is the vacuum freeze drying. More preferably, the drying is a vacuum freeze drying for 72 hours under 0.160 mBar and −30° C.

Preferably, the method for preparing the extracellular polysaccharide according to the present invention further includes the following steps:

(5) The crude product of extracellular polysaccharide obtained in step (4) is dissolved in 0.05 mol/L of Tris-HCl buffer with a pH value of 7.60. The EPS solution is chromatographed on a DEAE-Sepharose FF column. The linear gradient elution is conducted with the Tris-HCl buffer and the Tris-HCl buffer which contains 0.2-1.2 mol/L-NaCl in sequence. The flow rate is 2-6 mL/min. The eluent is monitored for carbohydrate content with the sulfuric acid-phenol method in the literature and The absorbance is measured at the wavelength of 490 nm. Based on tube numbers corresponding to the absorbance, the plot is drawn to obtain the elution curve A;

(6) The dialyzed aqueous solution corresponding to the single peak in elution curve A obtained in step (5) is collected. It is dialyzed with deionized water. The vacuum freeze drying is conducted to obtain a component B of extracellular polysaccharide;

(7) The component B of extracellular polysaccharide obtained in step (6) is dissolved in the Tris-HCl buffer to prepare the solution. The chromatography is conducted on DEAE-Sepharose CL-4B ion exchange column. The elution is conducted with the Tris-HCl buffer which contains 0.2-1.2 mol/L-NaCl. The flow rate is 2-6 mL/min. The eluent is monitored for carbohydrate content with the sulfuric acid-phenol method in the literature and the absorbance is measured at the wavelength of 490 nm. Based on tube numbers corresponding to the absorbance, the plot is drawn to obtain the elution curve B;

(8) The dialyzed aqueous solution corresponding to the single peak in elution curve B obtained in step (7) is collected. It is dialyzed with water. It is dried.

In the present invention, preferably, 50-200 mg of the crude product of extracellular polysaccharide obtained in step (5) is dissolved in 0.05 mol/L of Tris-HCl buffer with a pH value of 7.60 to prepare the solution with a concentration of 5-20 mg/mL. The preferred flow rate in step (5) is 3 mL/min. The DEAE-Sepharose FF column in step (5) is conventional in the art, preferably, D1.6×100 cm.

The preferred flow rate in step (7) is 3 mL/min. The DEAE-Sepharose CL-4B ion exchange column in step (7) is conventional in the art, preferably, D1.6×100 cm.

The "overnight" according to the present invention is a conventional term in the art. The preferred duration is 4-24 hours.

The sixth technical solution of the present invention is the use of the extracellular polysaccharide whose structural formula is shown in Formula (1) in promoting the proliferation of bifidobacteria.

Wherein, the extracellular polysaccharide is produced by *Paenibacillus*, and preferably, by *Paenibacillus bovis* sp. nov. BD3526 whose deposit number is CGMCC No. 8333. The extracellular polysaccharide is produced by the conventional method in the art, preferably, by the preparation method according to the present invention.

In the present invention preferably, the *bifidobacterium* spp. is a spieces existed in intestinal flora. The intestinal flora may come from human faecal samples, preferably, from faecal samples of 3-to-6-year-old children. Preferably, the bifidobacteria is *B. breve*, *B. longum*, or *B. infantis*, and more preferably, *B. breve*. According to common sense in the art, the preferred conditions mentioned above can be combined discretionarily to obtain preferred embodiments of the present invention.

All reagents and raw materials used in the present invention are commercially available.

The positive effects and progress of the present invention lie in that: the present invention provides a new strain of *Paenibacillus* spp. The taxonomic status of this strain is *Paenibacillus* spp. It is desirable to be named as *Paenibacillus bovis* sp. nov. in accordance with the nomenclature of International Committee Systematic Bacteriology (Gao et al., 2016, International Journal of Systematic and Evolutionary Microbiology). The discovery and utilization of the new strain enrich the available microbiological resources, and make contributions for better use of *Paenibacillus* in future. The *Paenibacillus* BD3526 according to the present invention can be used as a microbial therapeutic agent and can also be used for preparing extracellular polysaccharide. The present invention also provides an extracellular polysaccharide of *Paenibacillus* with a single component and a moderate degree of polymerization (DP=15-30). It can be obtained through the fermentation of *Paenibacillus* BD3526. It has similar effects to those of the commercialized fructooligosaccharide. Its preparation method is easy to conduct. It is conducive for purification. The inventors of the present invention have analyzed the physical & chemical properties and structural composition of the extracellular polysaccharide through rigorous experiments. The use for promoting the proliferation of *B. infantis* in vitro and adjusting the intestinal flora for adults in vitro is provided.

Deposit Information of Biological Materials

The *Paenibacillus* BD3526 of the present invention has been deposited in China General Microbiological Culture Collection Center (CGMCC) since Oct. 14, 2013, and the address for the deposition is Institute of Microbiology, Chinese Academy of Sciences, NO. 1-3 West Beichen Road, Chaoyang District, Beijing 100101, China. The deposit number for the strain is CGMCC No. 8333. The systematic name of the strain is *Paenibacillus* sp., with the strain designate of BD3526.

BRIEF DESCRIPTION OF THE DRAWINGS

Characteristics and beneficial effects of the present invention are illustrated below in combination of drawings.

DETAILED DESCRIPTION OF PREFERRED EMBODIMENTS

Figure 1:
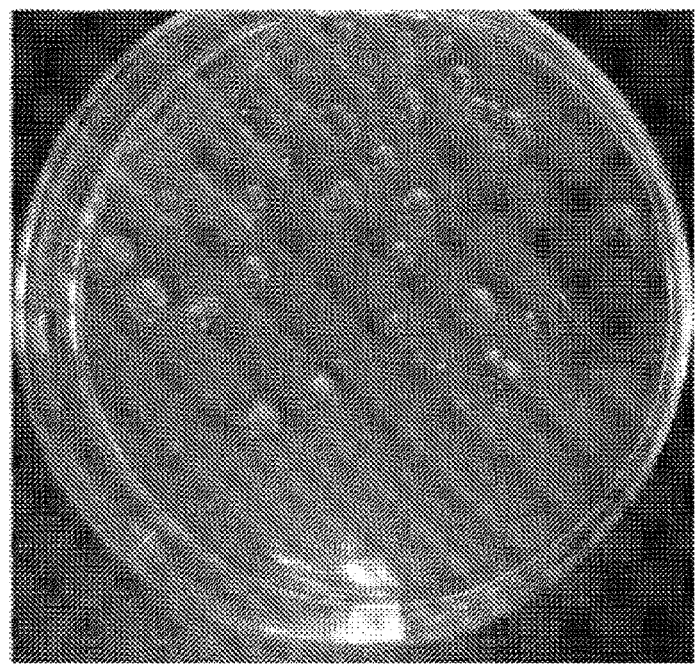
FIG. 1 shows the colonial morphology of new *Paenibacillus* strain BD3526 according to the present invention on TYC culture medium.

The present invention is further illustrated by means of examples below. However, the present invention is not thus limited within the scope of the examples. For experimental methods without any indicated specific conditions, conventional methods and conditions may be selected. Otherwise, the selection can be made in accordance with the instructions of the description of the commercial products. The room temperature according to the present invention refers to the temperature of operating room for the experiment and is usually 25° C. The "overnight" according to the present invention is a conventional term in the art, and the preferred duration for it is 4-24 hours.

*Paenibacillus hunanensis* FeL05$^T$ (ACCC 10718$^T$=CGMCC NO. 1.8907$^T$) and *Paenibacillus polymyxa* ATCC 842$^T$ (CGMCC No. 1.4261$^T$) are purchased from China General Microbiological Culture Collection Center (CGMCC).

Example 1 Acquisition of the New Microorganism According to the Present Invention 1 ml yak milk samples Collected at Damxung County, Tibet Autonomous Region, China is taken aseptically and subjected to serial dilution with sterile physiological saline. The diluent is spreaded onto the TYC agar evenly and then cultured for 24-48 hours under 30° C. Several snot-like, thread-drawing single colonies are selected and transferred respectively onto new TYC agar to obtain the purified colonies.

Example 2 Acquisition of the New Microorganism According to the Present Invention and the Characteristics Thereof Biolog microbial automatic detector (manufacturer: Biolog Inc.) identification assay: Biolog microbial automatic detector (manufacturer: Biolog Inc.) identification assay is based on the differences in metabolism of individual carbon resource by different microorganisms. 95 types of carbon sources or other chemical substances are selected and fixed together with the color developing agent onto the 96-well plate (A1 well is the negative control well). Bacterial suspension is inoculated and cultured for certain time. Characteristic fingerprint is generated by testing the turbidity caused by the growth of microorganisms. The final identification results are obtained by comparing the characteristic fingerprint with the standard strain profiles database.

1) A plurality of single colonies according to the above Example 1 is taken and inoculated onto the liquid TYC respectively. They are cultured for 24 hours under 30° C.

2) They are centrifuged for 20 min at 10000 r/min. The supernatant is discarded. 1 mL of sterilized saline is added. The mixture is shaken on a shaker for 5 min and centrifuged for 20 min at 10000 r/min to remove the carbon sources therein. The supernatant is discarded. 1 mL of sterilized saline is added, and the mixture is shaken on a shaker for 5 min.

3) The suspension is further diluted with sterile saline (NaCl, 0.85%) to make a suspension of absorbance at 590 nm at 0.13±0.02.

4) The above suspension is added onto the Biolog ECO microplate (150 μL/well). It is cultured under 20° C. The Biolog bacteria automatic readout device reads the data every 12 hours for 2 days continuously. The results are shown in Table 1.

TABLE 1

BIOLOG IDENTIFICATION RESULTS FOR STRAIN BD3526.

| | PROB | SIM | DIST | species |
|---|---|---|---|---|
| 1 | 0.535 | 0.535 | 6.927 | *Virgibacillus sediminis* |
| 2 | 0.117 | 0.117 | 7.531 | *Brachybacterium paraconglomeratum* |
| 3 | 0.102 | 0.102 | 7.716 | *Peanibacillus tundrae* |
| 4 | 0.095 | 0.095 | 7.802 | *Peanibacillus polymyxa* |

Three parameters should be taken into consideration to identify the results: Probabilities (PROB), Similarities (SIM), and Distances (DIS). SIM and DIS values are two important parameters, which indicate the matching degrees between the tested results and the corresponding data of the database. When DIS<5.0 and SIM>0.75, the matching is good. The results show that the identified SIM value of the strain BD3526 is 0.535<0.75, indicating a low matching degree with the data of the database. This shows that it has a significant difference from the strains of the database in terms of metabolic characteristic.

It probably is a new species of microorganism.

The strain BD3526 has been deposited in China General Microbiological Culture Collection Center (CGMCC) since Oct. 14, 2013, and the address for the deposition is: Institute of Microbiology, Chinese Academy of Sciences, NO. 1-3 West Beichen Road, Chaoyang District, Beijing 100101, China. The deposit number for the strain is: CGMCC No. 8333. The systematic name of the strain is *Paenibacillus bovis* sp. nov., with the designate of BD3526(Gao et al., 2016, International Journal of Systematic and Evolutionary Microbiology).

Example 3 Characteristics of the New Microorganism According to the Present Invention 1. Colony Characteristics:

A single colony of strain BD3526 is taken and transferred onto the TYC agar (agar). They are cultured aerobically at 30° C. for 24 hours, 36h, and 48h. The characteristics of colonies such as size, color, edge, embossment, smoothness, viscosity, and transparency are observed respectively. The results are shown in FIG. 1. The results show that on TYC agar, the strain BD3526 forms irregularly-edged, smooth, ropy, glossy-surfaced, and non-transparent colonies. The diameters are of 3-5 mm.

2. Morphological Observation and Physiological and Biochemical Characteristics:

Colonies on TYC solid culture medium (agar) for 24 hours are picked up for physiological and biochemical tests. The results show that the cells of the strain BD3526 are Gram-positive, with terminal spore in the shape of an oval, and not expanded. The parameters for physical and chemical reactions of BD3526 are shown in Table 2.

TABLE 2 results for physical and chemical tests on strain BD3526

| | | |
|---|---|---|
| Oxidase− | Catalase+ | β-galactosidase+ |
| arginine hydrolysis of− | double Lysine decarboxylase− | Ornithine decarboxylase+ |
| Urease− | Citrate utilization− | Nitrate reduction+ |
| Indole production− | VP reaction+ | $H_2S$ production− |
| Amylolysis+ | Esculin hydrolysis+ | Gelatin liquefaction+ |

3. API 50 CHB Identification Characteristics

The acid produced from fermentable carbohydrates by strain BD3526 is determined using API 50 CHB identification system (manufacturer: BioMe' rieux). In the reagent strips of API 50 CHB, different serial numbers correspond to different carbon sources. Meanwhile, the indicator is contained therein. Thus, if the corresponding carbon source is metabolized and acids are produced from the corresponding substrate, the pH value of the culture solution will decrease, and the color of the indicator will change. It is easy to observe and record.

1) The components of API 50 CHB basic culture medium are: 1 g of tryptone, 0.5 g of yeast extract, 2 g of ammonium sulfate, 0.18 g of phenol red, 10 ml of the inorganic salt base (Cohen-Bazire), and 1000 ml of phosphate buffer (pH7.8).

2) Freshly cultured colonies of BD3526 on TYC agar are picked and suspended into the sterilized saline, and transferred to the culture medium according to 1) to prepare a bacterial suspension with $OD_{600}$=0.4-0.6.

3) The bacterial suspension in 2) is then inoculated the small tubes on API 50 CHB test strips. A layer of sterilized paraffin oil is added into the tubes to cover the surface.

4) The inoculated tubes are cultured at 30° C. The change of color of the medium in the tubes (originally blue-purple, in the case of acid produced, the color would change to yellow) are recorded at 24 and 48 hours respectively.

The results for acid produced from fermented carbohydrates by strain BD3526 are shown in Tables 3 and 4.

TABLE 3

API 50 CHB identification results of strain BD3526

| | | | | |
|---|---|---|---|---|
| Control− | D-galactose+ | Glycerol− | Melibiose+ | Gentiobiose+ |
| Mannitol+ | D-glucosee+ | Maltose+ | Saccharose+ | D-lyxose− |
| Erythritol− | D-fructose+ | N-acetyl-glucosamine+ | Xylitol− | D-tagatose− |
| D-arabinose− | D-mannose+ | Amygdalin+ | Raffinose+ | D-fucose− |
| L-arabinose+ | L-sorbose− | Arbutin+ | Melezitose− | L-fucose− |
| D-ribose+ | L-rhamnose− | Esculin+ | Lactose+ | D-arabitol− |
| D-xylose+ | Dulcitol− | Salicin+ | Starch+ | L-arabitol− |
| L-xylose− | Iinositol− | Cellobiose+ | Glycogen+ | Gluconate+ |
| Adonitol− | α-methyl-D-mannoside− | α-methyl-glucoside− | 5-keto-gluconate− | 2-keto-gluconate+ |
| β-methyl-D-xylose+ | Sorbitol− | | | |

"+" refers to acid produced from sugar, and "−" refers to no acid produced.

TABLE 4

The acid producing profiles from fermentable carbohydrates by the strain BD3526 and its most genetically related *Paenibacillus* sp. strain

| Strains | 1 | 2 |
|---|---|---|
| Glycerol | − | w |
| Iinositol | − | w |
| Gluconate | + | w |
| α-methyl-glucoside | − | w |
| 2-keto-gluconate | + | − |
| Trehalose | w | + |

Note:
strain 1 refers to BD3526, and strain 2 refers to *Paenibacillus hunanensis* FEL05$^T$ (ACCC 10718[1]);
W REFERS TO "WEAK", i.e., WEAK POSITIVE.

As shown in Table 4, the strain BD3526 and *Paenibacillus hunanensis* FeL05$^T$ (ACCC 10718[1]) displayed different ability in terms of acid production from fermentable carbohydrates, indicating that the two strains belong to different species.

Example 4 Growth Characteristics of the New Microorganism According to the Present Invention 1. Growth Curve:

1) 30 mL of TYC liquid culture medium is added to the 100 mL Erlenmeyer flasks respectively, and sterilized at 121° C. for 15 minutes;

2) The freshly cultured colonies of strain BD3526 on TYC solid culture medium (agar) for 24 hours are inoculated into the TYC liquid culture medium as mentioned above, and incubated on a shaker at 30° C. for 20-24 hours to obtain the inocula.

Figure 2:
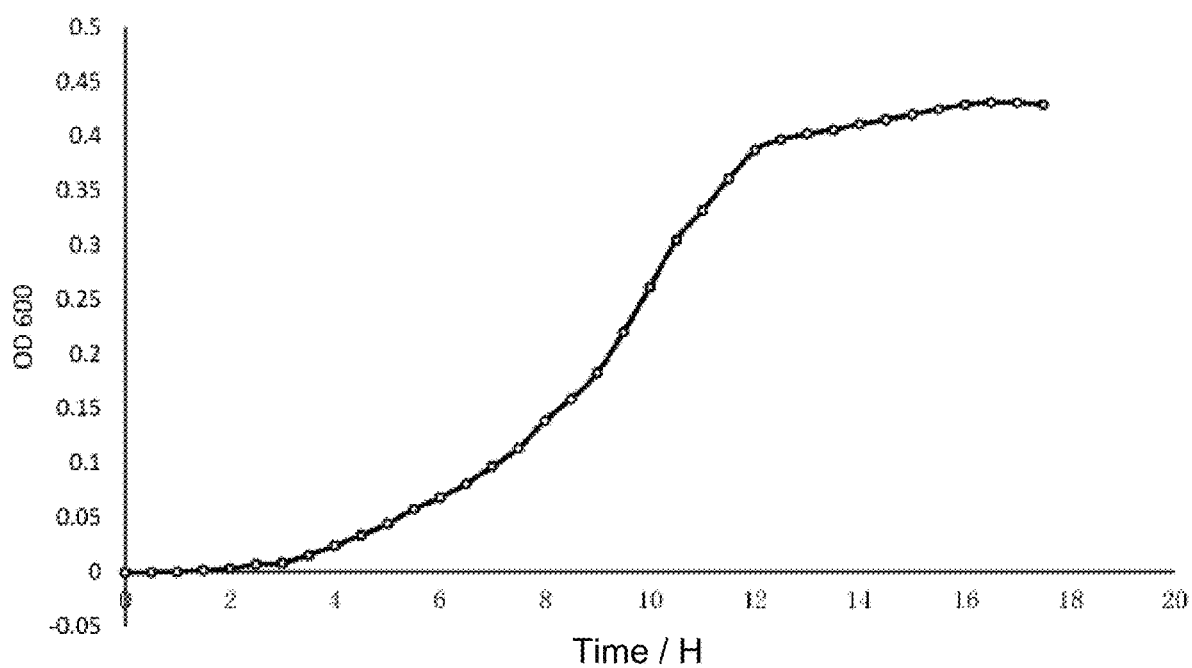
FIG. 2 shows the growth curve of *Paenibacillus* strain BD3526 according to the present invention. The horizontal axis refers to the time and the vertical axis refers to the OD value of the 100 μL-culture solution in 96-well plate at 600 nm.

3) The inocula of BD3526 obtained in 2) are transferred to the fresh TYC liquid culture at a ratio of 2% (v/v) and thoroughly mixed. The mixture is added into the wells on a costar 96-well sterile microwell plate, 150 μl for each well, and the experiment is taken out in triplicates, employing non-inoculated TYC liquid culture medium as the control. The absorbance of the wells at 600 nm is recorded at an interval of 30 min. The results are shown in FIG. 2.

2. Growth Temperature:

The inocula of BD3526 obtained in 2) is transferred to tubes containing 5 mL of the fresh TYC liquid culture at a ratio of 2% (v/v) and thoroughly mixed. The inoculated tubes are cultured in Water bath at 4° C., 15° C., 30° C., 37° C., 40° C. and 60° C., respectively, in triplicates for each temperature gradient. The turbidity of the tubes are recorded at 24 hours and 48h respectively to determine the growth of the strain BD3526, employing non-inoculated TYC liquid culture medium as the control. The obtained growth temperature range of strain BD3526 is 15-40° C., preferably, 30° C.

3. NaCl Tolerance for Growth

The inocula of BD3526 obtained in 2) is transferred to at a ratio of 2% (v/v) to tubes containing 5 mL of the fresh TYC liquid culture with a sodium chloride concentration of 0.0%, 2.0%, 5.0%, 7.0% and 10.0% respectively and cultured at 30° C. The turbidity of the tubes are recorded at 24 hours and 48h respectively to determine the growth of the strain BD3526, employing non-inoculated TYC liquid culture medium as the control. The results show that the NaCl tolerance for strain BD3526 is 10%.

4. pH Range for Growth

The pH value of the sterile TYC culture medium is adjusted to 3.0, 4.0, 5.0, 5.5, 6.0, 6.5, 7.0, 8.0, 8.5, 9.0 and 10.0 using sterile HCl and NaOH. The inocula of BD3526 obtained in 2) is transferred to at a ratio of 2% (v/v) to tubes containing 5 mL of the fresh TYC liquid culture of individual pH value and cultured at 30° C. The turbidity of the tubes are recorded at 24 hours and 48h respectively to determine the growth of the strain BD3526, employing non-inoculated TYC liquid culture medium with individual pH value as the control. The obtained pH range for growth of strain BD3526 is 5.5-8.5, and preferably is 6.0.

Example 5 the 16S Phylogenetic Characteristics for the New Microorganism According to the Present Invention The genomic DNA of strain BD3526 is obtained in accordance with the operation procedure for Gram-positive bacteria using TIANAMP Bacteria DNA Kit. The absorbance thereof is determined at 230 nm, 260 nm, and 280 nm. The A260: A280: A230 thereof is 1:0.510:0.445. The purity meets the requirements.

The fragment of 16S rDNA of strain BD3526 is amplified using 27F, 1492R-primer. The amplified fragments are purified and then ligated to the TA cloning vector of pMD19-T Simple Vector. Then, they are put into the water bath of 16° C. overnight. They are transformed into the competent cell of E. coli DH5a. They are spread onto the LB agar culture medium plate with ampicillin. They are cultured under 37° C. for 16-20 hours. The positive transformants are picked up. The positive transformants mentioned above are sent to JIE LI BIOLOGY Co. in Shanghai for sequencing. The results for sequencing are put into the database of NCBI and EzTaxon, and the most similar strain found through comparing is *Paenibacillus hunanensis* FeL05$^T$ with a similarity of 96.6%.

Sequences for the primer pair mentioned above are: for 1492R: TACCTTGTTACGACTT, and for 27F: AGAGTTTGATCCTGGCTCAG.

The result of gene sequencing of 16S rRNA of strain BD3526 is shown in SEQ ID NO. 1.

Figure 3:
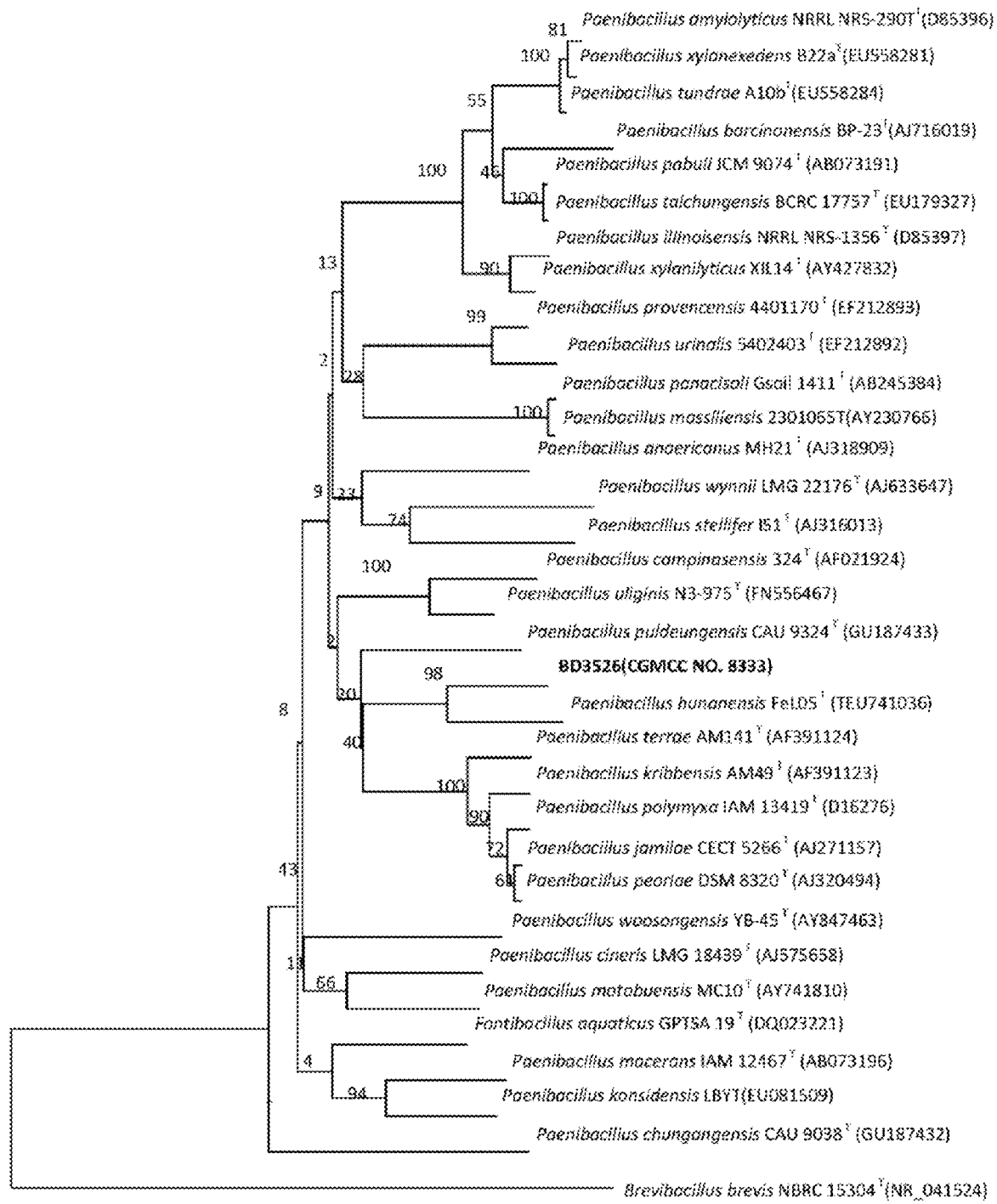
FIG. 3 shows the phylogenetic tree of 16S rRNA system of the new *Paenibacillus* strain BD3526 according to the present invention.

The sequence of 16S rRNA mentioned above is compared by using the software of CLUSTAL_X program (version 1.83) and the phylogenic tree is drawn by MEGA version 4.0.2. software. Using neighbor-joining for calculation with maximum-parsimony and maximum-likelihood for verification calculation, the bootstrap is set as 1000 cycles. The results are shown in FIG. 3. As shown in FIG. 3, through the analysis on phylogenetic tree of 16S rRNA gene, strain BD3526 shall be classified as the cluster of *Paenibacillus hunanensis*. However, the similarity between strain BD3526 and the type strain of *Paenibacillus hunanensis* is 96.6%. However, similarity of 16S rRNA gene lower than 97% is the threshold to discriminate different species strains in the same genus. Moreover, much evidence has been proven that for some bacteria with the similarity over 99% on gene sequence for 16S rRNA are still classified as different species. Thus, the strain BD3526 is likely to be a new species of microorganism with its other physiological and biochemical indexes to be verified.

Example 6 Characteristics on Fatty Acid Content for the New Microorganism According to the Present Invention The determination of total fatty acid of the strain BD3526 cells.

The following solutions are prepared: I, 45 g of sodium hydroxide is dissolved in 150 ml of methanol and 150 ml of distilled water; II, 190 ml of concentrated hydrochloric acid and 275 ml of methanol are dissolved in 135 ml of distilled water; III, 200 ml of normal hexane is mixed with 200 ml of ethyl ether homogeneously; IV, 10.8 g of sodium hydroxide is dissolved in 900 ml of distilled water; and V, saturated sodium chloride solution.

1) A certain amount of the bacterial culture is taken and added into a 8 ml-screwed glass tube. 1 ml of solution I is added. The screw cap of the tube is fastened and put into the boiling water bath for 5 min. It is taken out and shaken for 5 to 10 seconds. It is put into the boiling water bath for 25 min.

2) Once the sample tube is cooled down, 2 ml of solution II is added into it. The tube is capped, shaken. and bathed for 10 min at 80±1° C. with an accurate control. Then, it is cooled down with ice bath.

3) 1.25 ml of solution III is added into the solution mentioned above. It is rapidly shaken for about 10 min. The lower aqueous phase is discarded.

4) 3 ml of solution IV and 0.1-0.2 ml of solution V are added into the remaining organic phase. It is rapidly shaken for about 5 min. Two thirds of the upper organic phase is taken and put into the sample bottle of chromatography.

The HP6890 gas chromatograph is equipped with split/splitless inlet, hydrogenation flame ionization detector (FID) and HP gas chromatograph chemstation; the chromatographic column is Ultra-2 column with the length of 25 m, the inner diameter of 0.2 mm, and the liquid film thickness of 0.33 μm. The furnace temperature is two step programmed rising temperature. The initial temperature is 170° C. The temperature is raised up to 260° C. in the rate of 5° C./min and then raised up to 310° C. in the rate of 40° C./min and maintained for 1.5 min. The temperature at inlet is 250° C. and the carrier gas is hydrogen with the flow rate of 0.5 ml/min in split mode. The split ratio is 100:1. The sample size is 20. The temperature for test is 300° C., the flow rate of hydrogen is 30 ml/min, the flow rate of air is 216 ml/min and the flow rate of supplemental gas (nitrogen) is 30 ml/min.

The results show that the main cellular fatty acids of strain BD3526 are anteiso saturated fatty acid $C_{15:0}$, anteiso heptadecenoic saturated fatty acid, and hexadecanoyl saturated fatty acid. The percentages of the contents are 59.02%, 11.09%, and 7.66% respectively. The main fatty acid in accordance with the Paenibacillus is anteiso saturated fatty acid $C_{15:0}$. Both the type and the content of the fatty acid thereof are different from those of the similar strains. Therefore, the strain is determined as a different species from similar strains.

Example 7 Characteristics on G+C Mol % Content for the New Microorganism According to the Present Invention The determination for G+C mol % content of genomic DNA for strain BD3526.

The melting temperature (Tm) method is used. E. coli K12, AS 1.365 is used as the reference control. The device used is the Lambda35 UV/VIS Spectrometer of Perkin/Elmer. The temperature is controlled by PTP-1 temperature digital controller. The steps are as follows:

1) The sample DNA to be tested is diluted with 0.1×SSC such that its $OD_{260\ nm}$ value ranges from 0.3 to 0.4;

2) The OD value is recorded under 25° C. at the wavelength of 260 nm firstly. Then the temperature raising procedures is set up to raise the temperature from 65° C. to 95° C. at the rate of rising 1° C. per minute;

3) The raising of OD value indicates the beginning of denaturation. The temperature of cuvette and the OD value are recorded until the OD value remains unchanging, which indicates the completion of denaturation; and 4) The melting temperature (Tm) is obtained based on the thermal denaturation curve and calculating the G+C mol % content.

The calculation formula in 0.1×SSC solution is:

$$G+C\ mol\ \% = G+C\ mol\ \%\ AS_{1.365} + 2.08\ (Tm_{unknown} \rightarrow Tm_{AS1.365})$$

The Tm of E. coli K12, $AS_{1.365}$ determined in the test is 75.810° C.

The Tm value and G+C mol % of the strain:

The results of G+C mol % of strain BD3526 are shown in Table 5.

TABLE 5 the G + C mol % content for strain BD3526

| Strain number | Tm value, ° C. | G + C mol % |
|---|---|---|
| Control E coli kl2 | 75.810 | — |
| BD3526 | 74.024 | 47.48 |

The G+C mol % of strain BD3526 is 47.48%., The G+C mol % of Paenibacillus hunanensis FeL05$^T$ (ACCC 10718$^t$=CGMCC 1.8907$^T$=DSM22170$^T$) G+C mol % is 53.3%. The difference between the two strains is greater than 5%. The G+C content of Paenibacillus range is within 45-54 mol %. According to the "Common Bacteria Identification System Manual" (Dongfang Xiu, Cai Miaoying), the G+C content of Paenibacillus range is within 45-54 mol %; the difference of G+C mol % between the two strains is greater than 5%. Therefore, these two strains can be determined as different species (such determination can be made even if other characteristics are similar). Therefore, the strain BD3526 is classified as Paenibacillus sp. which belongs to a different species with respect to its most-similar strain Paenibacillus hunanensis FeL05$^T$ (ACCC 10718$^T$=CGMCC 1.8907$^T$=DSM 22170$^T$).

Example 8 Hybridization Experiment for the New Microorganism According to the Present Invention The hybridization experiment was carried out between the strain BD3526 and the reference strain with the most related genetic relationship as well as the type strain in the genus of Paenibacillus.

Referring to the results of 16S rRNA, DNA-DNA hybridization experiment between strain BD3526 and the species of Pamibacillus hunanensis FeL05$^T$ (ACCC 10718$^T$=CGMCC 1.8907$^T$=DSM 22170$^T$) with the most related genetic relationship is conducted, and DNA-DNA hybridization experiment between strain BD3526 and the type strain Pamibacillus polymyxa ATCC 842$^T$ (=CGMCC 1.4261$^T$=DSM 36$^T$=KCTC 3858$^T$) of Pamibacillus is conducted.

The method of liquid phase renaturation rate is used. The device used is the Perkin Elmer Lambda35 UV/VIS Spectrophotometer. The temperature is controlled by PTP-1 Peltier System digital temperature controlling system. The steps are as follows.

1) DNA sample processing: the DNA sample is extracted as described in Example 5 above. Before the experiment, it is ice-bathed and zapped with the ultrasonic wave of 40W for 24 minutes (the setting is: zapping for 3 seconds/pausing for 3 seconds). The concentration of DNA sample is $OD_{260}$ nm of 2.0. The DNA sample is cut into fragments of $2-5\times10^5$ dalton.

2) The DNA samples (A, B) to be tested are precisely prepared using 0.1×SSC respectively into a status where the $OD_{260}$ nm value range is 1.8-2.0. The $OD_{260}$ nm value for both of them shall be consistent (as accurate as 0.001).

3) After entering the UV Winlab program (manufacturer: Perkin Elmer), the method window appears. The "Time-Driven" (TD) method in the method window is selected. Proper parameters are set on the "Timed, Inst. Sample." setting page. The wavelength for determination is 260 nm and the total time for determination is set as 30 minutes. The optimal renaturation temperature (TOR) on the basis of the G+C mol %. The temperature of cuvette is kept stable at the optimal renaturation temperature. In 2×SSC reaction liquid, the optimal renaturation temperature is calculated by the formula: TOR=0.51×(G+C) mol %+47.

4) 400 μl of the DNA samples of each of the two strains is added into two centrifugal tubes separately. 200 μl of the DNA samples of each of the two strains is added into the same centrifugal tube to form the mixed sample.

5) Before testing, the single DNA sample and mixed DNA sample should be degenerated for 15 min under 100° C. through PTP-1 temperature-control system (manufacturer: Perkin Elmer), respectively. They are cooled down to the optimal renaturation temperature. The $OD_{260}$ nm value is recorded. The reading does not stop until 30-min of the reaction. The temperature of samples should not be lower than TOR during the whole process. Finally, a straight line showing a gradually decreased absorbance value with time is be obtained.

6) Based on the software UV Winlab, select "Slope" in "Algorithm" column therein to obtain the renaturation rate (V), namely, slope ("V" usually represents the reduced amount of absorbance per minute).

7) The homogenous hybridization rate is calculated by the formula.

Homogenous hybridization rate $(H)$ %$=4Vm-(Va+Vb)/2\sqrt{Va}\sqrt{Vb}-100\%$

The results of DNA-DNA hybridization is as follows:
BD3526/*Paenibacillus hunanensis* FeL05$^T$ (repeat for three times):
H %=39.82% (I);
H %=41.60% (II); and
H %=42.10% (III).
BD3526/*Paenibacillus polymyxa* ATCC 842$^T$ (repeat for three times):
H %=41.62% (I);
H %=46.60% (II); and
H %=48.60% (III).

The results show that the DNA homology between the strains BD3526 and *Paenibacillus hunanensis* FeL05$^T$ (ACCC 10718$^T$=CGMCC 1.8907$^1$=DSM 22170$^1$) is 39.82~42.10%. With respect to the type strain *Paenibacillus polymyxa* ATCC 842$^T$ (=CGMCC 1.4261$^T$=DSM 36$^T$=KCTC 3858$^T$) of *Paenibacillus*, the DNA homology is 41.62-48.60%. Based on "Bergey's Manual of Determinative Bacteriology", under the optimum conditions, if the DNA homology is greater than 70%, they belong to the same species; and if the DNA homology is greater than 20%, they belong to the same genus. Together with the data of Examples 2, 3, 4, 5 and 6, it is determined that the strain BD3526 belong to a new species of *Paenibacillus*. The taxonomic status of this strain is originally proposed as *Paenibacillus damxungensis* sp. nov., and finally named as *Paenibacillus bovis* sp. nov., in accordance with the nomenclature of International Committee Systematic Bacteriology (Gao et al., 2016, International Journal of Systematic and Evolutionary Microbiology). Moreover, the strain BD3526 is selected as the type strain of this species.

Example 9 Use of the New Microorganism According to the Present Invention

As shown in FIG. 1, the colonies of strain BD3526 are viscous, indicating a high yield of extracellular polysaccharide thereof. The single colonies mentioned above are picked up and inoculated onto the TYC liquid culture medium for fermentation. The products are obtained after ethanol precipitation. They are identified as polysaccharides. The polysaccharide is produced by the natural fermentation of strain BD3526. It is safe, nontoxic, and may serve as an emulsifier, thickener, stabilizer, gelatinizer, and etc. for industrial applications. Strain BD3526 can also be used directly in the form of a microbial therapeutic agent.

Example 10 Preparation for Extracellular Polysaccharide of the Strain BD3526

(1) The cultivation of *Paenibacillus* and the preparation for fermentation broth
10.0 mg of the freeze-dried powder of *Paenibacillus* BD3526 is dissolved with 1 mL of sterile distilled water. One loop of the suspension is picked and streaked on the solid polysaccharide-producing culture medium (the solid polysaccharide-producing culture medium is consisted of 1.2% of agar, 10% of saccharose, 1% of casein tryptone, 5% of yeast extract, 5% of K$_2$HPO$_4$, 0.034% of CaCl$_2$), and distilled water, wherein the percentages refer to the mass percentages with respect to the solid-polysaccharide-producing culture medium). It is aerobically cultured for 24 hours at 30° C.

The single colony formed on the solid polysaccharide-producing culture medium is picked up and transferred into the liquid polysaccharide-producing culture medium (consisting of 10% of saccharose, 1% of casein tryptone, 0.5% of yeast extract, 0.5% of K$_2$HPO$_4$, 0.034% of CaCl$_2$), and distilled water, wherein the percentages refer to the mass percentages with respect to the liquid polysaccharide-producing culture medium). It is cultured for 24 hours under 30° C. to obtain the inocula. The inocula is transferred into fresh liquid polysaccharide-producing culture medium at a ratio of 2% (v/v). It is cultured for 72 hours under 30° C. to obtain the fermentation broth.

(2) The preparation of the crude product of extracellular polysaccharide in the fermentation broth
(2.1) The fermentation broth obtained in step (1) is heated under 100° C. for 10 minutes. It is cooled down to 25° C. The pH value is adjusted to 4.60 with food-grade lactic acid or hydrochloric acid. It stands for 4 hours. It is centrifuged for 10 min (14000 g). The supernatant is taken. 3 volumes of 95%-ethanol solution to that of the supernatant are added under gentle stirring and the mixture stands overnight. It is centrifuged for 10 min (14000 g). The precipitates are collected. The percentage refers to the mass percentage of the ethanol with respect to the ethanol solution.

(2.2) The precipitate obtained in step (2.1) is dissolved in distilled water at 60° C. to reach a final concentration of 0.8%. The percentage refers to the mass-volume percentage of the solution of precipitates. When the solution is cooled down to 25° C., trichloroacetic acid is added into the solution to a final concentration of 4% (w/v). The solution stands for 16 hours under 4° C. It is centrifuged or filtered to remove precipitates. The supernatant is dialyzed using a dialysis bag (Spectrumlabs, U.S.) with a molecular weight cut-off of 1000 Da against distilled water for 72 hours. Water is changed every 12 hours. The retentate is obtained.

Figure 4:
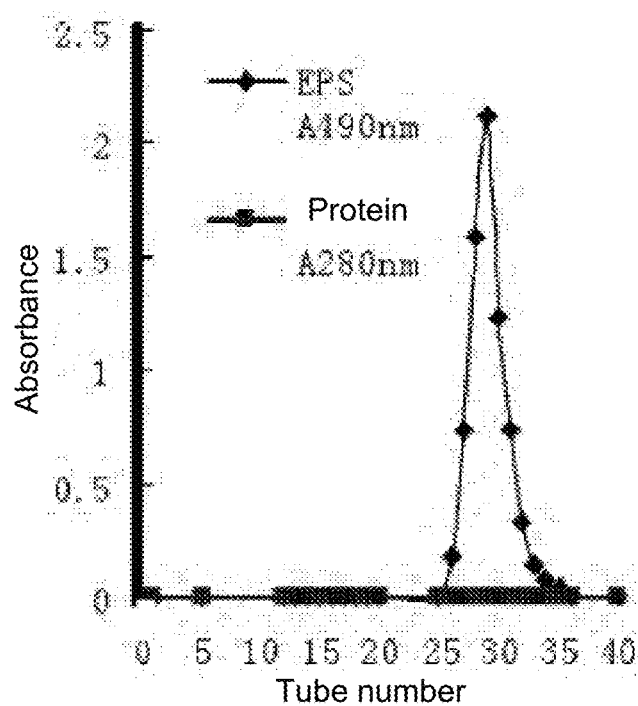
FIG. 4 shows the absorbance value OD at A490 nm and A280 nm of the crude product of extracellular polysaccharide of the *Paenibacillus* strain BD3526 according to the present invention.

(2.3) The retentate obtained in step (2.2) is vacuum freeze dried under the condition of 0.160 mBar, −30° C. for 72 hours to obtain the crude product of extracellular polysaccharide. The purity of the crude extracellular polysaccharide is checked by determining its absorbance at 490 nm via sulfuric—phenol method or directly at 280 nm. The results are shown in FIG. 4. A490 nm is the characteristic peak of polysaccharide. A280 nm is the characteristic peak of protein. The results show that there is only one symmetric peak at 490 nm, indicating that the content of crude proteins in extracellular polysaccharide is ignorable. Meanwhile, based on the calibration curve of standards (glucose or bovine serum albumin respectively) at A490 nm and A280 nm, it is known that the crude product of extracellular polysaccharide has a high purity. The extracellular polysaccharide content is 95.7%. The percentage refers to the mass percentage of the crude product of extracellular polysaccharide.

Example 11 Purification for the Crude Product of Extracellular Polysaccharide (1) 100 mg of the crude product of the extracellular polysaccharide obtained in Example 10 is dissolved in Tris-HCl buffer (0.05 mol/L, pH 7.60) to prepare the solution with a concentration of 10.0 mg/mL. The chromatography is performed on the DEAE-Sepharose FF column (D1.6X 100 cm) (GE Healthcare). The linear gradient elution is conducted with the Tris-HCl buffer and in turn the Tris-HCl buffer (0.05 mol/L, pH 7.60) which contains 0.2-1.2 mol/L-NaCl. The flow rate is 3 mL/min. The liquid is collected in tubes (6 mL per tube). The sulfuric acid—phenol method (Dubois, M., K. A. Gilles, J. K. Hamilton, P. A. Rebers, and F. Smith, 1956. Colorimeteric method for determination of sugars and related substances. Anal. Chem. 28:350-356) is used for tracking and monitoring. The absorbance is determined at the wavelength of 490 nm (i.e. the characteristic wavelength for the polysaccharide). Based on tube numbers corresponding to the absorbance, the plot is drawn to obtain the elution curve A. The data of the elution curve are shown in Table 6. Thus, the primarily purified component of polysaccharide is obtained. That is, peak F1 (refer to FIG. 5) may comprise two or more different polysaccharide components. Further purification for verification is required.

TABLE 6 data of elution curve A

| Tube number | $OD_{490}$ NM |
|---|---|
| 2 | 0.0711 |
| 6 | 0.0597 |
| 10 | 0.0539 |
| 14 | 0.0758 |
| 18 | 0.062 |
| 22 | 0.06 |
| 26 | 0.063 |
| 28 | 0.083 |
| 29 | 0.093 |
| 30 | 0.112 |
| 31 | 0.1845 |
| 32 | 0.3545 |
| 33 | 0.7526 |
| 34 | 1.0895 |
| 35 | 1.1524 |
| 36 | 1.0752 |
| 37 | 0.8605 |
| 38 | 0.4123 |
| 39 | 0.2715 |
| 40 | 0.1628 |
| 41 | 0.098 |
| 42 | 0.085 |
| 43 | 0.078 |
| 47 | 0.068 |
| 51 | 0.07 |
| 52 | 0.0656 |
| 55 | 0.0731 |
| 58 | 0.0664 |
| 63 | 0.0671 |
| 67 | 0.0723 |
| 71 | 0.0689 |
| 75 | 0.0742 |
| 79 | 0.0853 |
| 81 | 0.0725 |
| 82 | 0.0834 |
| 83 | 0.0923 |
| 84 | 0.0808 |
| 85 | 0.0946 |
| 86 | 0.0989 |
| 87 | 0.0873 |
| 88 | 0.0622 |
| 89 | 0.0676 |
| 90 | 0.0648 |

Figure 5:
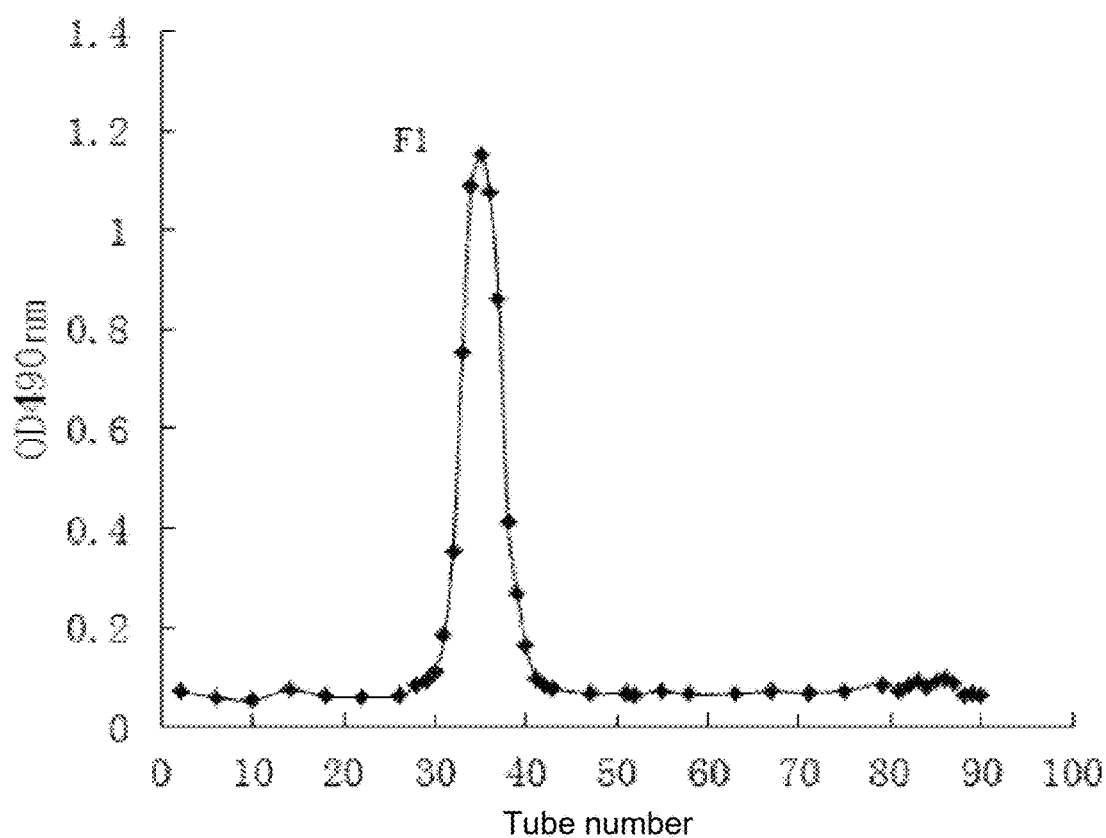
FIG. 5 shows the elution curve on DEAE-Sepharose ion exchange column for the crude product of extracellular polysaccharide of the *Paenibacillus* strain BD3526 according to the present invention; wherein, the vertical axis refers to the absorbance value OD of the eluent through sulfuric acid—phenol colorimetric method at n=490 nm, and the horizontal axis refers to the tube numbers.

(2) The aqueous solution obtained through the elution from the tube with the number corresponding to the single peak (F1) obtained in FIG. 5 in step (1) is collected. It is dialyzed with a dialysis tube with a molecular cut-off of 1000 Da against deionized water for 72 hours. The vacuum freeze drying (0.160 mBar, −30° C.) is conducted for 72 hours to obtain the component B of extracellular polysaccharide.

Figure 6:
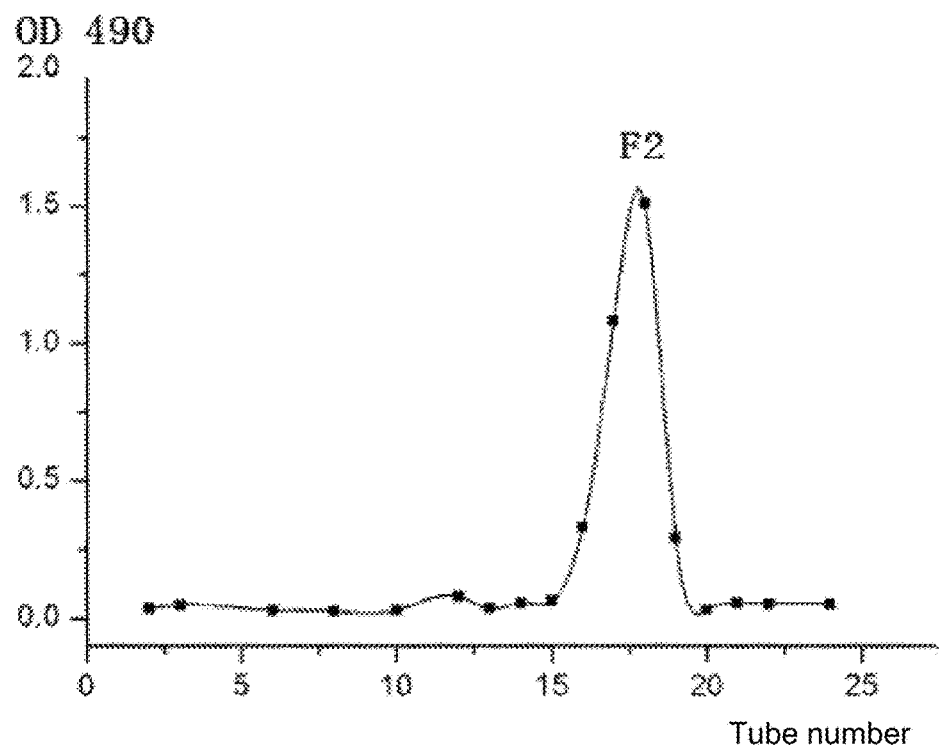
FIG. 6 shows the elution curve on a Sepharose CL-4B SEC column based on size exclusion chromatography, of the peak of charged part (F1) of the extracellular polysaccharide of the *Paenibacillus* strain BD3526 according to the present invention; wherein, the vertical axis refers to the absorbance value OD of the eluent through sulfuric acid—phenol colorimetric method where n=490 nm, and the horizontal axis refers to the tube numbers.

(3) The component B of extracellular polysaccharide obtained in step (2) is dissolved in the Tris-HCl buffer to prepare the solution with the concentration of 10.0 mg/mL. The chromatography is performed on the ion exchange column (the packing is DEAE-Sepharose CL-4B; column: D1.6X 100 cm, GE Healthcare). The elution is conducted using the Tris-HCl buffer which contains 0.2-1.2 mol/L NaCl. The flow rate is 3 mL/min. The eluent is collected in tubes (6 mL per tube). The sulfuric acid—phenol method is used for tracking and monitoring. The absorbance at the wavelength of 490 nm is determined. Based on the tube numbers corresponding to the absorbance, the plot is drawn to obtain the elution curve B. The experimental results are shown in FIG. 6. There is only one single peak F2 in FIG. 6, indicating that only one component of polysaccharide is contained. Moreover, F2 is the component of polysaccharide obtained through the further purification of the primarily purified component F1 of polysaccharide.

(4) The aqueous solution obtained through chromatography from the tubes with numbers corresponding to the single peak (F2) in FIG. 6 in step (3) is collected. It is dialyzed with a 1000-Da-dialysis bag in deionized water for 72 hours. The vacuum freeze drying is conducted under the condition of 0.160 mBar, −30° C. for 72 hours to obtain the purified extracellular polysaccharide, wherein the polysaccharide content is 100% with no proteins contained. The percentage refers to the mass percentage of the extracellular polysaccharide.

The purified extracellular polysaccharide prepared in Example 10 and 11 will be used in examples 14 to 18.

Example 12 Preparation for Extracellular Polysaccharide of the Strain BD3526

I Preparation for Polysaccharide of Strain BD3526

(1) The cultivation of *Paenibacillus* and the preparation for fermentation broth 10.0 mg of the freeze-dried powder of *Paenibacillus* BD3526 is dissolved in 0.1 mL of sterile distilled water. The strain is picked up with an inoculating loop and streaked on the solid polysaccharide-producing culture medium (consisting of 1.2% of agar, 10% of saccharose, 1% of casein tryptone, 0.5% of yeast extract, 0.5% of $K_2HPO_4$, 0.034% of $CaCl_2$), and distilled water, wherein the percentages refer to the mass percentages with respect to the solid polysaccharide-producing culture medium) and cultured aerobically at 30° C. for 24 hours.

The single colonies are picked up from the solid polysaccharide-producing culture medium and transferred into the liquid polysaccharide-producing culture medium (consisting of 10% of saccharose, 1% of casein tryptone, 0.5% of yeast extract, 0.5% of $K_2HPO_4$, 0.034% of $CaCl_2$), and distilled water, wherein percentages refer to the mass percentages of the liquid polysaccharide-producing culture medium) for a 24 hours-culture under 30° C. to obtain the seed liquid. It is cultured for 24 hours under 30° C. to obtain the inocula. The inocula is transferred into fresh liquid polysaccharide-producing culture medium at a ratio of 2% (v/v). It is cultured for 72 hours under 30° C. to obtain the fermentation broth.

(2) The preparation of the crude product of extracellular polysaccharide in the fermentation broth (2.1) The fermentation broth obtained in step (1) is heated under 95° C. for 10 min. Once cooled down to 15° C., the pH value is adjusted to 4.4 with food-grade lactic acid or hydrochloric acid. It stands for 3 hours. It is centrifuged for 10 min (14000 g) The supernatant is taken. 4 volumes of 80%-ethanol solution of the supernatant is added under gentle stirring and the mixture is left to stand overnight. It is centrifuged for 10 min (14000 g). The precipitates are collected. The percentage refers to the mass percentage of the ethanol solution.

(2.2) The precipitate obtained in step (2.1) is dissolved in distilled water whose temperature is 50° C. to reach a final concentration of 0.5%. The percentage refers to the mass-volume percentage of the solution of precipitate. Once cooled down to 25° C. trichloroacetic acid is added to the solution, such that the final percentage of trichloroacetic acid is 10%. The percentage refers to the mass-volume percentage of the solution. The solution stands for 16 hours under 4° C. It is centrifuged or filtered to remove precipitates. The supernatant is obtained. The supernatant is dialyzed with a dialysis tube (Spectrumlabs, U.S.) with a molecular weight cut-off of 1000 Da against distilled water for 72 hours. The water is changed every 12 hours to obtain the dialyzed aqueous solution.

(2.3) The dialyzed aqueous solution obtained in step (2.2) is vacuum freeze dried directly. It is vacuum freeze dried under the condition of 0.160 mBar, −30° C. for 72 hours to obtain the crude product of extracellular polysaccharide. The absorbance at A490 nm by sulfuric acid-phenol method and A280 nm are determined to determine the purity.

II Purification for the Crude Product of Extracellular Polysaccharide (1) 100 mg of the crude product of the extracellular polysaccharide obtained in Example 10 is dissolved in the Tris-HCl buffer (0.05 mol/L, pH 7.60) to prepare a solution with the concentration of 5 mg/mL. The chromatography is performed on the DEAE-Sepharose FF column (D1.6X 100 cm) (GE Healthcare). The linear gradient elution is conducted with the Tris-HCl buffer and in turn the Tris-HCl buffer (0.05 mol/L, pH7.60) which contains 0.2-1.2 mol/L NaCl. The flow rate is 2 mL/min. The liquid is collected in tubes (6 mL per tube). The sulfuric acid—phenol method is used to determine the absorbance at the wavelength of 490 nm (i.e. the characteristic wavelength for polysaccharide). Based on the tube numbers corresponding to the absorbance, the plot is drawn to obtain the elution curve A. Thus, a primarily purified component of polysaccharide is obtained, namely, the single peak F1.

(2) The aqueous solution obtained from the tube with the number corresponding to the single peak (F1) through elution in step (1) is collected. It is dialyzed with a 1000 Da-dialysis bag in deionized water for 72 hours. The vacuum freeze drying (0.160 mBar, −30° C.) is conducted for 72 hours. The component B of extracellular polysaccharide is obtained.

(3) The component B of extracellular polysaccharide obtained in step (2) is dissolved in the Tris-HCl buffer to prepare a solution with the concentration of 5 mg/mL. The chromatography is performed on ion exchange column (wherein the packing is DEAE-Sepharose CL-4B; column: D1.6X 100 cm, GE Healthcare). The elution is conducted with the Tris-HCl buffer which contains 0.2-1.2 mol/L NaCl. The flow rate is 2 mL/min. The liquid is collected in tubes (6 mL per tube). The sulfuric acid—phenol method is used for tracking and monitoring. The absorbance is determined at the wavelength of 490 nm. Based on the tube numbers corresponding to the absorbance, the plot is drawn to obtain the elution curve B. Thus, the further purified component of polysaccharide is obtained on the basis of component F1, namely, the single peak F2.

(4) The aqueous solution obtained from the tube with the number corresponding to the single peak (F2) through chromatography in step (3) is collected. It is dialyzed with a 1000 Da-dialysis bag in deionized water for 72 hours. The vacuum freeze drying (0.160 mBar, −30° C.) is conducted for 72 hours to obtain the purified extracellular polysaccharide.

Example 13 Preparation and Purification for Extracellular Polysaccharide of the Strain BD3526

I Preparation for Polysaccharide of Strain BD3526

(1) The cultivation of *Paenibacillus* and the preparation for fermentation broth 10.0 mg of the freeze-dried powder of *Paenibacillus* BD3526 is dissolved with 1 mL of sterile distilled water. One loop of the suspension is picked and streaked on the solid polysaccharide-producing culture medium (the solid polysaccharide-producing culture medium is consisted of 1.2% of agar, 10% of saccharose, 1% of casein tryptone, 5% of yeast extract, 5% of $K_2HPO_4$, 0.034% of $CaCl_2$), and distilled water, wherein the percentages refer to the mass percentages with respect to the solid-polysaccharide-producing culture medium). It is aerobically cultured for 24 hours at 30° C.

The single colony formed on the solid polysaccharide-producing culture medium is picked up and transferred into the liquid polysaccharide-producing culture medium (consisting of 10% of saccharose, 1% of casein tryptone, 0.5% of yeast extract, 0.5% of $K_2HPO_4$, 0.034% of $CaCl_2$), and distilled water, wherein the percentages refer to the mass percentages with respect to the liquid polysaccharide-producing culture medium). It is cultured for 24 hours under 30° C. to obtain the inocula. The inocula is transferred into fresh liquid polysaccharide-producing culture medium at a ratio of 1% (v/v). It is cultured for 72 hours under 30° C. to obtain the fermentation broth.

(2) The preparation of the crude product of extracellular polysaccharide in the fermentation broth (2.1) The fermentation broth obtained in step (1) is heated under 100° C. for 30 min. It is cooled down to 25° C. The pH value is adjusted to 4.8 with food-grade lactic acid or hydrochloric acid. It stands for 5 hours. It is centrifuged for 10 min (14000 g). The supernatant is taken. 80%-ethanol solution with the volume twice as much as that of the supernatant is added into the centrifuged supernatant mentioned above. It stands overnight. It is centrifuged for 10 min (14000 g). The precipitates are collected. The percentage refers to the mass percentage of the ethanol with respect to the ethanol solution.

(2.2) The precipitates obtained in step (2.1) is dissolved with distilled water whose temperature is 80° C. to reach a final concentration of 1%. The percentage refers to the mass-volume percentage of the solution of precipitates. When the solution is cooled down to 25° C., the trichloroacetic acid is added, such that the final percentage of the trichloroacetic acid is of 6%. The percentage refers to the mass-volume percentage of the solution. The solution stands for 16 hours under 4° C. It is centrifuged or filtered to remove precipitates. The supernatant is obtained. The supernatant is dialyzed using a dialysis bag (Spectrumlabs, U.S.) which has a molecular weight cut-off of 1000 Da in distilled water for 72 hours. The water is changed every 12 hours. The dialyzed aqueous solution is obtained.

(2.3) The dialyzed aqueous solution obtained in step (2.2) is vacuum freeze dried directly. It is vacuum freeze dried under the condition of 0.160 mBar, −30° C. for 72 hours to obtain the crude product of extracellular polysaccharide. The absorbance at A490 nm and A280 nm is determined to determine the purity.

II Purification for the Crude Product of Extracellular Polysaccharide (1) 100 mg of the crude product of the extracellular polysaccharide obtained in Example 10 is dissolved in the Tris-HCl buffer (0.05 mol/L, pH7.60) to prepare a solution with the concentration of 20 mg/mL. The chromatography is performed on the DEAE-Sepharose FF column (D1.6X 100 cm) (GE Healthcare). The linear gradient elution is conducted with the Tris-HCl buffer and in turn the Tris-HCl buffer (0.05 mol/L, pH7.60) which contains 0.2-1.2 mol/L NaCl. The flow rate is 6 mL/min. The liquid is collected in tubes (6 mL per tube). The sulfuric acid—phenol method is used to determine the absorbance at the wavelength of 490 nm (i.e. the characteristic wavelength for polysaccharide). Based on tube numbers corresponding to the absorbance, the plot is drawn to obtain the elution curve A. Thus, the primarily purified component of polysaccharide is obtained, namely, the single peak F1.

(2) The aqueous solution obtained from the tube with the number corresponding to the single peak (F1) through the elution in step (1) is collected. It is dialyzed with a 1000 Da-dialysis bag in deionized water for 72 hours. The vacuum freeze drying (0.160 mBar, −30° C.) is conducted for 72 hours to obtain the component B of extracellular polysaccharide.

(3) The component B of extracellular polysaccharide obtained in step (2) is dissolved in the Tris-HCl buffer to prepare a solution with the concentration of 20 mg/mL. The chromatography is performed on the ion exchange column (the packing is DEAE-Sepharose CL-4B; column: D1.6X 100 cm, GE Healthcare). The elution is conducted using the Tris-HCl buffer which contains 0.2-1.2 mol/L NaCl. The flow rate is 6 mL/min. The liquid is collected in tubes (6 mL per tube). The sulfuric acid—phenol method is used for tracking and monitoring. The absorbance at the wavelength of 490 nm is determined. Based on the tube numbers corresponding to the absorbance, the plot is drawn to obtain the elution curve B. Thus, a further purified component of polysaccharide is obtained on the basis of component F1, namely, the single peak F2. (4) The aqueous solution obtained from the tube with the number corresponding to the single peak (F2) through chromatography in step (3) is collected. It is dialyzed with a 1000-Da-dialysis bag in deionized water for 72 hours. The vacuum freeze drying is conducted under the condition of 0.160 mBar, −30° C. for 72 hours to obtain the purified extracellular polysaccharide.

Example 14: Structural Analysis for Extracellular Polysaccharide (1) Infrared (FI-IR) Analysis 2.0 mg of the purified extracellular polysaccharide obtained in Example 11 and KBr are ground and tabulated. The infrared multispectral scan (Xu Guangtong, Yuan Hongfu, Lu Wanzhen, et al, Development of Modern Near Infrared Spectroscopic Techniques and Its Applications, SPECTROSCOPY AND SPECTRAL ANALYSIS, 2000, 02:134-142) (infrared spectrometer: Thermo Fisher Scientific) is conducted within the area of 4000-500 $cm^{-1}$.

Figure 7:
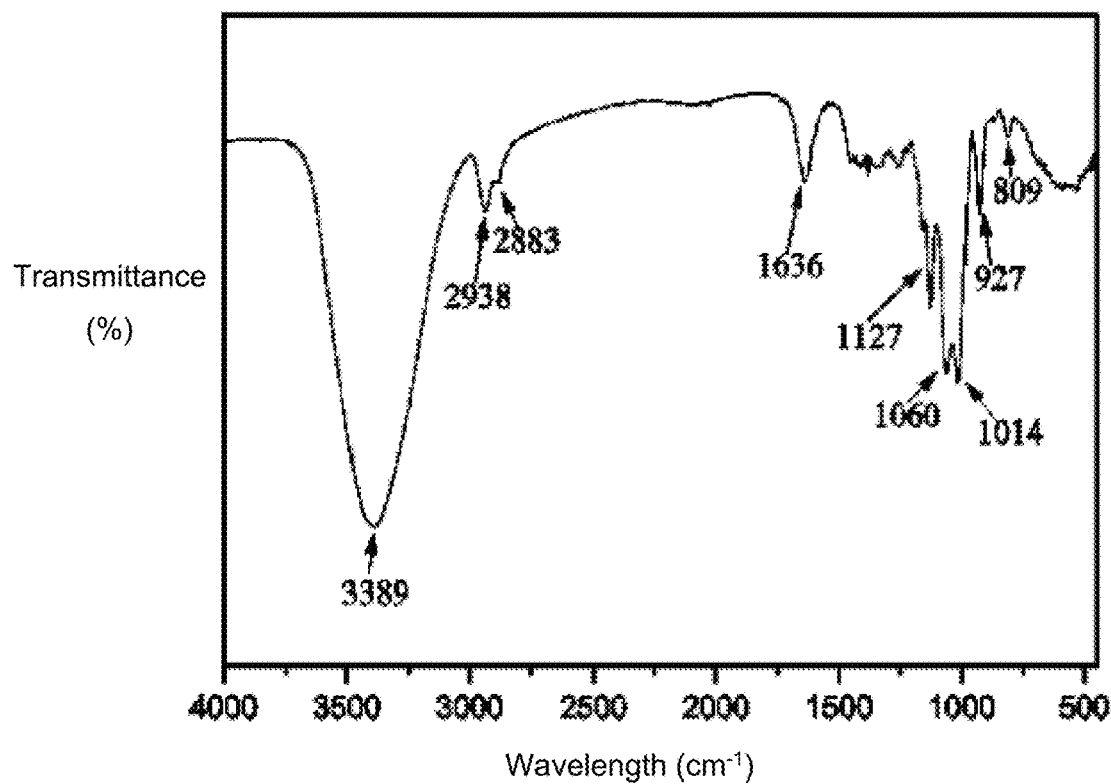
FIG. 7 shows the infrared spectrum of the purified extracellular polysaccharide of the *Paenibacillus* strain BD3526 according to the present invention.

The infrared spectrogram is shown in FIG. 7. Detailed data are shown in Table 7.

TABLE 7 data of infrared spectrogram

| Wave number of absorption peak $cm^{-1}$ | Functional group | Vibration mode | Type of characteristic absorption peak |
|---|---|---|---|
| 3389 | —OH | OH stretching vibration | |
| 2937 | —CH | C—H stretching vibration | characteristic peak of polysaccharide |
| 2882 | —CH | C—H stretching vibration | characteristic peak of polysaccharide |
| 1635 | —OH | OH bending vibration | |
| 1127 | C—O—C (on ring) | C—O stretching vibration | |
| 1014 | —OH | OH deformation vibration | |
| 1060 | —OH | OH deformation vibration | |
| 927 | furan ring | symmetrical stretching vibration of furan ring | |
| 809 | —CH | C—H deformation vibration of furan ring | |

Figure 8:
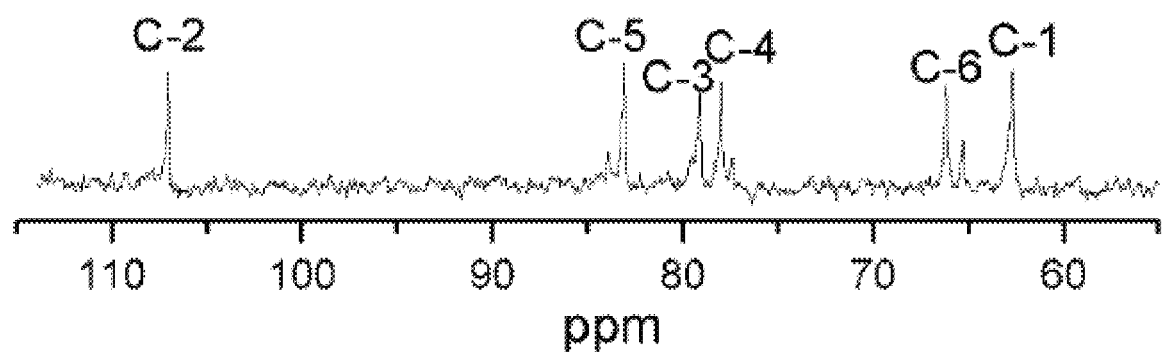
FIG. 8 shows the $^{13}$C-NMR spectrum of the purified extracellular polysaccharide of the *Paenibacillus* strain BD3526 according to the present invention.

(2) Nuclear Magnetic Resonance (NMR) Analysis 10 mg of the purified extracellular polysaccharide obtained in Example 11 is dissolved in 1 mL of heavy water (D20). The $^1$H-NMR and $^{13}$C-NMR spectrums are determined using JNM-A500 (manufactured by Nippon Denshi). The $^{13}$C-NMR spectrum is shown in FIG. 8. The specific data of $^1$H-NMR spectrum are as follows: δ (3.538)-(3.585) ppm is H-6b, δ (3.661)-(3.692) ppm is H-lb; δ (3.748)-(3.793) ppm is H-1a; δ (3.894) ppm is H-6a; δ (3.935) ppm is H-5; 6 (4.082)-(4.132) ppm is H-4; and δ (4.082)-(4.132) ppm is H-4, δ (4.184)-(4.205) ppm is H-3. In FIG. 8, δ (62.67) is C-1, δ (66.46)-δ (66.25) is C-6; δ(77.38)-δ (77.98) is C-4; δ (79.07) is C-3; δ (83.07)-δ (83.92) is C-5; and δ (79.07) is C-2. Therefore, comparing with the standard spectrum for glycosidic bond of fructose, these data indicate that the extracellular polysaccharide refers to the levan jointed with β(2→6) glycosidic bond. Meanwhile, the results of NMR data also indicate that the purified extracellular polysaccharide obtained in Example 11 comprises no characteristic peaks of a non-carbohydrate structure such as protein, sulfide and amidogen, namely, it is a pure levan with no impurities (for example, protein) contained.

Example 15: Molecular Weight Distribution of the Purified Extracellular Polysaccharide (1) The standard samples with different molecular weights are sampled consecutively. The retention time TR is recorded. A standard curve is drawn, wherein the horizontal axis refers to retention time RT and the vertical axis refers to 1 gM, so as to get the regression equation between the molecular weight and the retention time RT.

(2) The purified extracellular polysaccharide to be tested is dissolved in ddH$_2$O to reach a concentration of 10 g/L. Sampling is conducted to obtain TR. The relative molecular weights of the samples are calculated through regression equation.

Chromatographic conditions are as follows:

Chromatographic instrument: Viscotek TDAmax (Waters China)

Detector: refractive index detector (Waters China)

Chromatographic column: GPCmax™ range: 2000-20000000 Dalton (Waters China)

Moving phase: 0.1 mol/L NaNO$_3$

Figure 9:
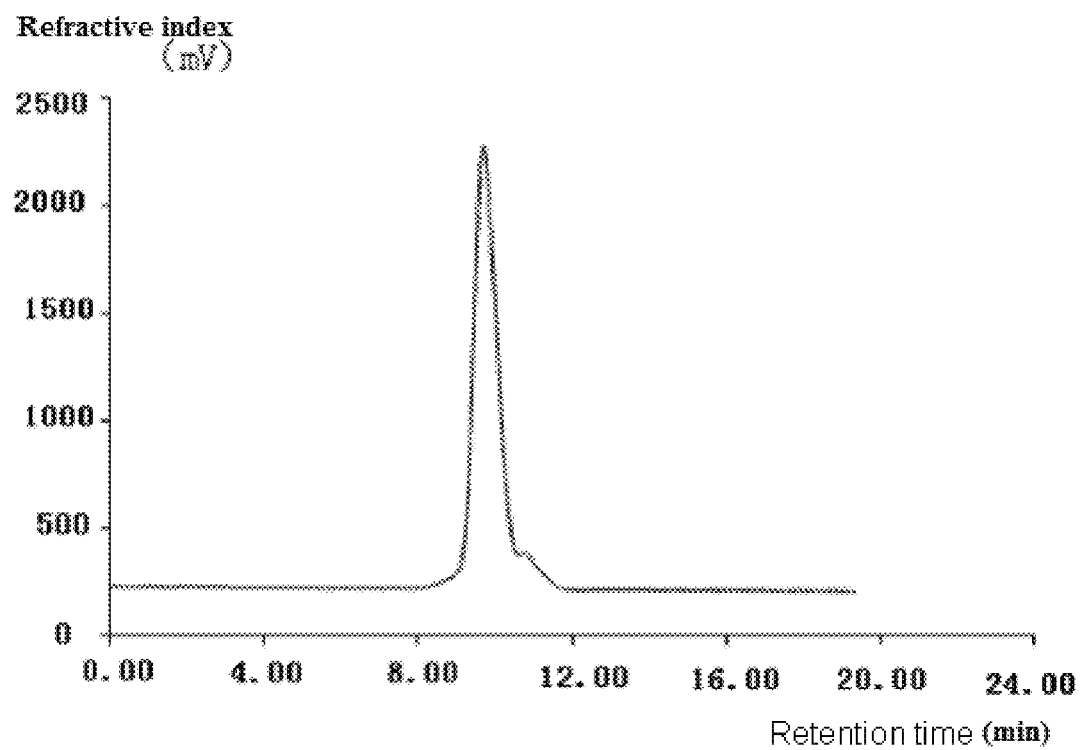
FIG. 9 shows the molecular weight determined by liquid chromatography for the purified extracellular polysaccharide of the *Paenibacillus* strain BD3526 according to the present invention; wherein, the vertical axis refers to intensity of the refractive index reflecting the content of polysaccharides in the elents and the horizontal axis refers to the retention time (min).

Column temperature: 30° C.; Flow rate: 1 mL/min; Concentration of sample: 10 mg/mL The results of molecular weight distribution of the polysaccharide mentioned above are shown in FIG. 9. The results indicate that a single peak appears at the retention time of 9.7 min, showing that the obtained exopolysaccharide is homogenous. The range of average molecular weight of the polysaccharide mentioned above is 2500-5000 Da. About 90% of the extracellular polysaccharide molecules have a molecular weight within the range of 2500-5000 Da, wherein the percentage refers to the mole percentage of the extracellular polysaccharide.

Figure 10:
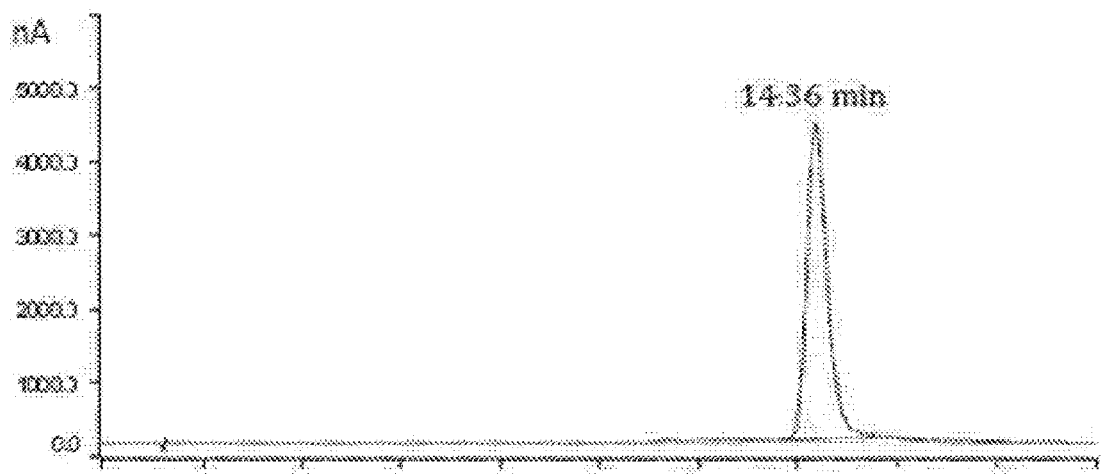
FIG. 10 shows the monosaccharide composition for the purified extracellular polysaccharide of the *Paenibacillus* strain BD3526 according to the present invention; wherein, the vertical axis refers to the intensity of refractive index caused by the existence of monosaccharide, and the horizontal axis refers to the retention time. (a) shows the diagram of fructose (reference), and (b) shows the acidic hydrolysate of the purified extracellular polysaccharide of the *Paenibacillus* strain BD3526.
Figure 10:
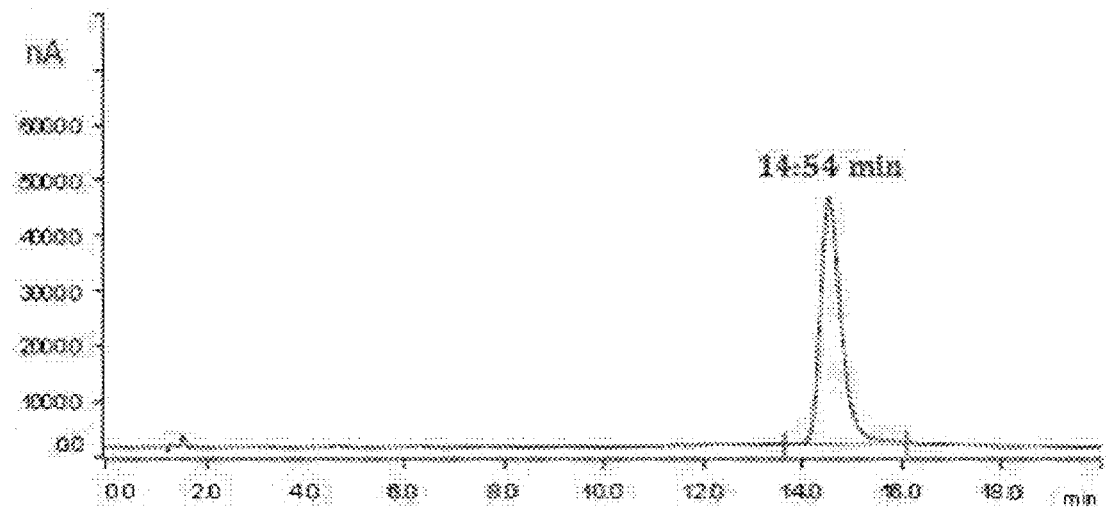

Example 16: Analysis on Monosaccharide Composition of the Purified Extracellular Polysaccharide 10 mg of the purified extracellular polysaccharide is dissolved in 2 mL of the 0.05 mol/L H$_2$SO$_4$ solution. It is hydrolyzed for 2 hours under 80° C. to obtain the hydrolysate A. The hydrolysate A is diluted 100 times to obtain the hydrolysate B. The monosaccharide composition of hydrolysate B is analyzed by the high performance ion chromatography (HPAEC-PAD) (Suo Hui, The Primary Structure of Garlic Fructan (D). Jinan University, Guangdong, 2010) The determination conditions for ion chromatography are: chromatographic column: (Carbopac, China): Carb1, 4×250 mm; flow rate: 1.0 mL/min; sample size: 20 μL; detector: pulsed amperometric detector (Carbopac, China), gold electrode; temperature for determination: 30° C. The isocratic elution is conducted with 15 mM NaOH solution. The experimental results are shown in FIG. 10. The results show that a peak of about 4200 nA is produced by fructose at 14:36 min. The sample of the purified extracellular polysaccharide produces a peak at 14:54 min. The peak appears at the same time as that of fructose. This indicates that the purified extracellular polysaccharide is consisting of single fructose.

The results of examples 14 to 16 show that the constitutional repeating unit of the extracellular polysaccharide is fructose. The fructose residual is linked by means of →2,6-fructose→2,6-fructose. The extracellular polysaccharide obtained is referred to levan and the structural formula of the extracellular polysaccharide is shown as Formula (1),

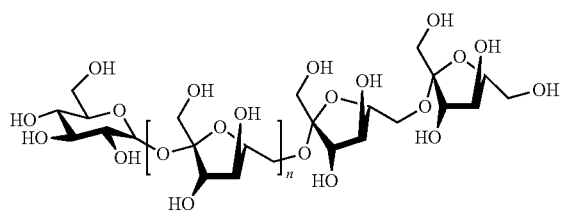

(1)

wherein, n=15~30, and the extracellular polysaccharide has an appearance of pure white filament or powder.

Example 17 the Proliferation of B. infantis Promoted by Extracellular Polysaccharide In Vitro (1) The faeces of 30 infants (with the age range from 6 to 24 months, excluding those who have intestinal diseases or taking antibiotic drugs recently) are collected. The standard culture solution of fecal flora is prepared in accordance with the method of Minekus et al (Models of the gastrointestinal tract to study microbial interactions Original Research Article Biology of Growing Animals, 2005, 2:142-154).

(2) Certain amount of standard ileum efflux culture medium (SIEM, with 0.047 g/L pectin, 0.047 g/L xyloglucan, 0.047 g/L arabinogalactan, 0.047 g/L amylose, 0.392 g/L starch, 24.0 g/L casein, 17.0 g/L Tween 80, 24.0 g/L bacto peptone, 0.4 g/L oxgall, and 0.2 g/L cysteine) is added into a 96-well microtitration plate. Then, the 0.1% of the standard culture solution of fecal flora is added. The percentage refers to the volume percentage of the standard ileum efflux culture medium. Then, 0.4% of the purified extracellular polysaccharide ("BD3526 extracellular polysaccharide" for short) obtained in Example 11 and 0.4% of the commercialized fructooligosaccharide (FOS for short) are added into different wells among the 96 wells respectively. The final volume of liquid in each well is 1.5 mL. Meanwhile, the blank control is arranged. They are anaerobically cultured for 8 hours under 37° C. The percentage refers to the mass-volume percentage of the final volume of the liquid in a well of the 96-well microtitration plate.

Figure 11:
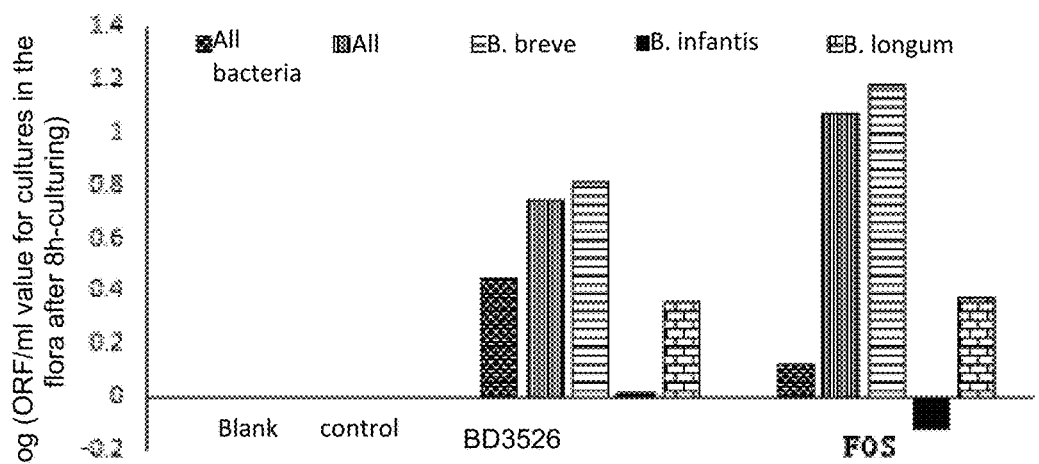
FIG. 11 shows the graph of the in-vitro proliferation of *Bifidobacterium infantis* facilitated by the purified extracellular polysaccharide of the *Paenibacillus* strain BD3526 according to the present invention. Wherein, the blank control group refers to the blank control (i.e. the relative bacterial flora content of the in-vitro culture solution of infant feces without polysaccharide added); the extracellular polysaccharide of BD3526 refers to the relative increase value of the bacterial flora content of the in-vitro culture solution of infant feces with 0.4% (w/v) of the extracellular polysaccharide of the *Paenibacillus* strain BD3526 according to the present invention added; FOS refers to the relative increase in the bacterial flora content of the in-vitro culture solution of infant feces with 0.4% (w/v) of the commercialized fructooligosaccharide added.

(3) Once the cultivation is completed, the fermentation broth is mixed with 250 μL of lysis buffer, 2504, of zirconium bead liquid (0.1 mm) and 200 μL of phenol solution. Then they are homogenized on the bead beater (BIO SPEC Inc. U.S.) for twice (2 minutes for each time). The DNA is extracted with DNA Kit (TIANGEN BIOTECH CO., LTD). Then, PCR-intestinal microarray detection method (SALAZAR N, GUEIMONDE M, HERNANDEZ-BARRANCO A M, et al. Exopolysaccharides produced by intestinal Bifidobacterium strains act as fermentable substrates for human intestinal bacteria. Applied and environmental microbiology, 2008, 74(15): 4737-45.) is used to analyze the number of floras in samples with respect to that of the blank control (standard solution of fecal flora cultured without adding polysaccharide). The experimental results are shown in FIG. 11 and Table 8 (wherein, the log (ORF/mL) value of all floras in the blank control is defined as 0). As shown in FIG. 11, comparing with the blank control group, Paenibacillus BD3526 EPS (e.g, FOD) can also promote the proliferation of the bifidobacteria in infants' fecal flora, especially the proliferation of B. breve. As shown in Table 8, comparing with the blank control, the number of bifidobacteria in floras is increased for both samples with added FOS and BD3526 extracellular polysaccharide. Especially for B. breve, the increment of number (log (ORF/mL) value) of the sample with added BD3526 extracellular polysaccharide is 0.81, which almost reaches that (1.18) of the sample with added FOS. For B. longum, the increment of number (log (ORF/mL) value) of the sample with added BD3526 extracellular polysaccharide is 0.36, which approximates that (0.37) of the sample with added FOS added.

TABLE 8 the number of strains in the flora cultured for 8 hours
The increased log (ORF/mL) value of the flora in
samples with respect to the blank control

| Treatment for culturing | All bacteria | All bifidobacteria | B. breve | B. infantis | B. Longum |
|---|---|---|---|---|---|
| Blank control group | 0 | 0 | 0 | 0 | 0 |
| BD3526 extracellular polysaccharide | 0.448 | 0.74 | 0.81 | 0.017 | 0.36 |
| FOS | 0.12 | 1.07 | 1.18 | −0.121 | 0.37 |

Example 18 Effect of Adjusting the Composition of Intestinal Flora for Adults In Vitro (1) The faeces of 30 healthy adults (male or female, with the age range from 23 to 25, excluding those who have intestinal diseases or taking antibiotic drugs recently). They are dissolved in pH7.3-phosphate buffer (8 g/L-NaCl, 0.2 g/L-KCl, 1.15 g/L-NaHPO$_4$, and 0.2 g/L-KH$_2$PO$_4$) and mixed uniformly. It is added into the culture system at a volume ratio of 1:10. Then, 0.4% of the purified extracellular polysaccharide (BD3526EPS for short) obtained in Embodiment 11 and 0.4% of the commercialized fructooligosaccharide (FOS for short) are added into the culture system respectively. Meanwhile, the blank control is arranged. They are anaerobically cultured for 24 hours under 37° C. The percentages refer to the mass-volume percentages of the culture system.

Figure 12:
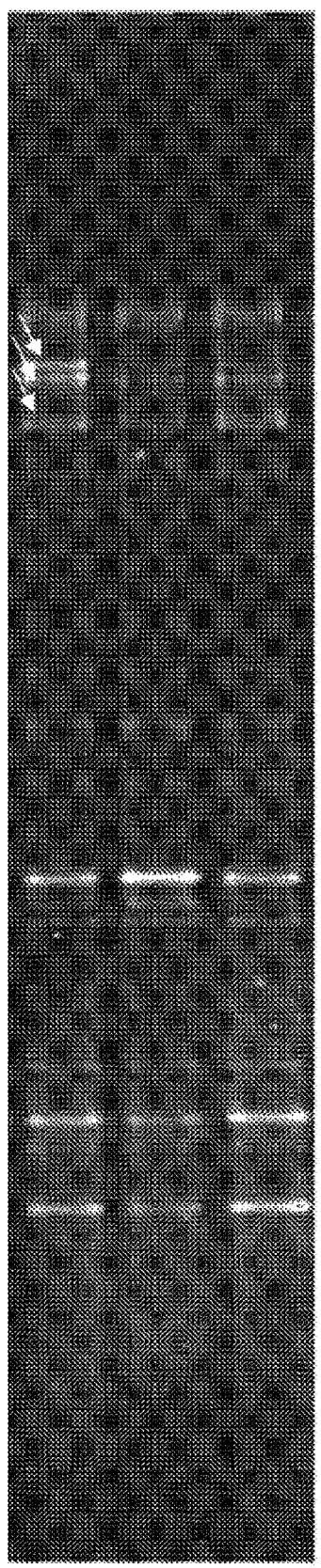
FIG. 12 shows the PCR-DGGE diagram of V3 area for total bacteria of the fecal cultures. Wherein, the blank control group refers to the sample of fecal cultures with no polysaccharide added, FOS refers to the fecal cultures with the commercialized fructooligosaccharide added, and BD3526 EPS refers to the fecal cultures with the purified extracellular polysaccharide of the *Paenibacillus* strain BD3526 according to the present invention added.

(2) Once the culture is completed, the phenol-chloroform method (ERCOLINI D, HILL P J, DODD C E. Bacterial community structure and location in Stilton cheese. Applied and environmental microbiology, 2003, 69(6): 3540-8.) is used to extract the DNA of the cultures and fecal flora. Then PCR-DGGE (denaturing gel gradient electrophoresis) method is used (Analysis of inherited and acquired mutations using PCR and denaturing gradient gel electrophoresis (DGGE) Mutation Research/Environmental Mutagenesis and Related Subjects, Volume 252, Issue 2, 1991, 175-176. A.-L. Borresen, E. Hovig, B. Smith-SOrensen, S. Lystad, A. Bragger) to analyze the composition of the flora of the samples. That is, the universal primer 357F (as shown in SEQ ID NO. 4) (5'-TACGGGAGGCAGCAG-3'), 518R (as shown in SEQ ID NO. 5) (5'-ATTACCGCGGCTGCTGG-3') of 16S rDNA for the bacteria, and GC-clamp (as shown in SEQ ID NO. 6) (5'-CGCCCGCCGCGCGCG-GCGGGCGGGGCGGGGGCACGGGGGGCC-3') are used. The PCR amplification system is 25 μL (8.5 μL of sterile double distilled water, 1 μL of each of primer 518R, 1 μL of GC-357F, 2 μL of template, and 12.5 μL of 2× Plus-Mix). The amplification protocol is: 5 min under 94° C.; then 30s under 94° C., 30s under 56° C., 40s under 68° C., 35 cycles; at last, 10 min under 72° C. for extension. The amplification products are added onto the gel with a polyacrylamide concentration of 8% (wt) and a denaturing gradient range from 40% (wt) to 60% (wt). Electrophoresis is conducted under 60° C. using the voltage of 75V with 1×TAE as the electrophoresis buffer. Once the electrophoresis is completed, stain the gel with ethidium bromide. Photographs are taken with the gel imaging system. The results are shown in FIG. 12. The stripes pointed by arrows in FIG. 12 are significantly brighter than those of the FOS group and the blank control group which indicates that BD3526EPS can promote the proliferation of bacteria of this kind in human intestinal flora, and has the ability to adjust the composition of human intestinal flora.

Although descriptions above on embodiments of the present invention are given, those skilled in the art shall understand that all these are just examples of illustration and various changes or modifications may be executed in these embodiments without departing from the principle and essence of the present invention. Therefore, the protection scope of the present invention shall be limited by the Claims attached.

What is claimed is:

1. A *Paenibacillus* sp., wherein a deposit number of the *Paenibacillus* sp. is CGMCC No. 8333, and G+C content of the *Paenibacillus* sp. is 47.48 mol %.

2. The *Paenibacillus* sp. of claim 1, wherein main cellular fatty acids of the *Paenibacillus* sp. comprise anteiso saturated fatty acid $C_{15:0}$, anteiso heptadecenoic saturated fatty acid, and hexadecanoyl saturated fatty acid, a content ratio of the anteiso saturated fatty acid $C_{15:0}$ is 59.02%, a content ratio of the anteiso heptadecenoic saturated fatty acid is 11.09%, and a content ratio of the hexadecanoyl saturated fatty acid is 7.66%.

3. A method for culturing the *Paenibacillus* sp. of claim 1, comprising the following steps: inoculating the *Paenibacillus* onto a culture medium; culturing at a temperature of 15-40° C. with a pH value of 5.5-8.5.

4. The method of claim 3, wherein the temperature for the culturing is 30° C.

5. The method of claim 3, wherein the pH value for the culturing is 3.0.

6. The method of claim 4, wherein the pH value for the culturing is 3.0.

7. The method of claim 3, wherein the culture medium for the culturing further comprises less than 10% of NaCl by a mass percentage.

8. The method of claim 4, wherein the culture medium for the culturing further comprises less than 10% of NaCl by a mass percentage.

9. The method of claim 5, wherein the culture medium for the culturing further comprises less than 10% of NaCl by a mass percentage.

10. The method of claim 3, wherein the culturing is shaking culturing.

11. The method of claim 4, wherein the culturing is shaking culturing.

12. The method of claim 5, wherein the culturing is shaking culturing.

13. The method of claim 6, wherein the culturing is shaking culturing.

14. The method of claim 3, wherein an inoculation ratio of the culturing is 2% by a volume percentage.

15. The method of claim 3, wherein the culture medium is TYC culture medium.

16. The method of claim 3, wherein the culturing is conducted under aerobic conditions.

* * * * *